US010546652B2

(12) United States Patent
Jung et al.

(10) Patent No.: US 10,546,652 B2
(45) Date of Patent: Jan. 28, 2020

(54) COMPUTATIONAL SYSTEMS FOR BIOMEDICAL DATA

(75) Inventors: Edward K. Y. Jung, Bellevue, WA (US); Royce A. Levien, Lexington, MA (US); Robert W. Lord, Seattle, WA (US); Mark A. Malamud, Seattle, WA (US); Lowell L. Wood, Jr., Bellevue, WA (US)

(73) Assignee: Gearbox LLC, Bellevue, WA (US)

( * ) Notice: Subject to any disclaimer, the term of this patent is extended or adjusted under 35 U.S.C. 154(b) by 2237 days.

(21) Appl. No.: 11/541,478

(22) Filed: Sep. 29, 2006

(65) Prior Publication Data

US 2008/0082500 A1   Apr. 3, 2008

(51) Int. Cl.
*G16H 10/20* (2018.01)

(52) U.S. Cl.
CPC .................................. *G16H 10/20* (2018.01)

(58) Field of Classification Search
CPC ....................................................... G16H 10/20
USPC .......................................................... 702/19
See application file for complete search history.

(56) References Cited

U.S. PATENT DOCUMENTS

| | | | |
|---|---|---|---|
| 5,910,421 A | 6/1999 | Small, Jr. et al. |
| 5,916,818 A | 6/1999 | Irsch et al. |
| 6,140,047 A | 10/2000 | Duff et al. |
| 6,190,909 B1 | 2/2001 | Levinson et al. |
| 6,219,674 B1 | 4/2001 | Classen |
| 6,317,700 B1 | 11/2001 | Bagne |
| 6,493,637 B1 | 12/2002 | Steeg |
| 6,548,245 B1 | 4/2003 | Lilly et al. |
| 6,602,509 B1 | 8/2003 | Saint-Remy et al. |
| 6,759,234 B1 | 7/2004 | Gefter et al. |
| 7,024,369 B1 | 4/2006 | Brown et al. |
| 7,118,869 B2 | 10/2006 | Blumenfeld et al. |
| 7,177,675 B2 | 2/2007 | Suffin et al. |
| 7,198,895 B2 | 4/2007 | Mohanlal |
| 7,489,964 B2 | 2/2009 | Suffin et al. |
| 7,491,553 B2 | 2/2009 | Brown et al. |
| 7,732,135 B2 | 6/2010 | Hershey et al. |
| 2001/0020240 A1 | 9/2001 | Classen |
| 2002/0055855 A1 | 5/2002 | Cule et al. |
| 2002/0083080 A1 | 6/2002 | Classen |
| 2002/0187158 A1 | 12/2002 | Mahler et al. |
| 2003/0046110 A1 | 3/2003 | Gogolak |
| 2003/0074225 A1 | 4/2003 | Borsand et al. |
| 2003/0087320 A1 | 5/2003 | Vojdani |
| 2003/0099979 A1 | 5/2003 | Ohtani et al. |
| 2003/0104453 A1 | 6/2003 | Pickar et al. |
| 2003/0163353 A1 | 8/2003 | Luce et al. |
| 2003/0177512 A1 | 9/2003 | Avner |
| 2004/0024772 A1 | 2/2004 | Itai |
| 2004/0093331 A1 | 5/2004 | Gardner et al. |
| 2005/0196752 A1 | 9/2005 | Blumenfeld et al. |
| 2006/0008834 A1 | 1/2006 | Margus et al. |
| 2006/0015952 A1 | 1/2006 | Filvaroff |
| 2006/0111292 A1 | 5/2006 | Khan et al. |
| 2006/0188913 A1 | 8/2006 | Krieg et al. |
| 2006/0200480 A1 | 9/2006 | Harris et al. |
| 2007/0054282 A1 | 3/2007 | Liew |
| 2007/0183978 A1 | 8/2007 | Preuss et al. |
| 2007/0288256 A1* | 12/2007 | Speier .............................. 705/1 |
| 2007/0294113 A1 | 12/2007 | Settimi |
| 2008/0058407 A1 | 3/2008 | Baron et al. |
| 2009/0074711 A1 | 3/2009 | Glennie |
| 2010/0235184 A1 | 9/2010 | Firminger et al. |
| 2010/0235185 A1 | 9/2010 | Firminger et al. |
| 2010/0241448 A1 | 9/2010 | Firminger et al. |
| 2010/0241454 A1 | 9/2010 | Firminger et al. |
| 2010/0324936 A1 | 12/2010 | Vishnubhatla et al. |
| 2011/0112860 A1 | 5/2011 | Kehr |

FOREIGN PATENT DOCUMENTS

JP          03-292898          12/1991

OTHER PUBLICATIONS

Hansen et al., "The Variability of Individual Tolerance to Methotrexate in Cancer Patients" Br. J. Cancer (1971) vol. 2, pp. 298-305.*
"A Single-blind Randomized Phase 3 Trial of ALIMTA (pemetrexed) plus Cisplatin versus Cisplatin Alone in Patients with Malignant Pleural Mesothelimoa"; Eli Lilly and Company; bearing dates of Nov. 15, 2004 and 2004; pp. 1-13; located at http://www.clinicalstudyresults.org/documents/company-study_36_0.pdf.
U.S. Appl. No. 11/647,533, Jung et al.
U.S. Appl. No. 11/647,531, Jung et al.
"Allergen Online: Home of the farrp allergen protein database"; bearing dates of Jan. 2007 and 2006; pp. 1-3; University of Nebraska, Lincoln, NE; located at http://www.allergenonline.com; printed on Feb. 16, 2007.
"Allergy Testing—Physician Overview", MDS Diagnostic Services, bearing a date of Nov. 9, 2006, p. 1, located at http://www.mdsdx.com/pring/MDS_Diagnostic_Services/Patients/TestInfo/Special/allergy3.asp.
Amoli, M.M., et al., "Polymorphism in the STAT6 gene encodes risk for nut allergy"; Genes and Immunity; bearing a date of Feb. 13, 2002; pp. 220-224; vol. 3; Nature Publishing Group.
Asero, Riccardo, et al.; "IgE-Mediated food allergy diagnosis: Current status and new perspectives"; Mol. Nutr. Food Res; bearing dates of 2007; Jul. 31, 2006 and Aug. 4, 2006; pp. 135-147; vol. 51.
Banik, Utpal, Ph.D., et al., "Cross-reactivity Implications for Allergy Diagnosis", News & Views, bearing a date of 2006, pp. 13-16, Issue 2, located at www..dpcweb.com-under Technical Documents, News & Views, 2006, Issue 2.
Bataille, Veronique, "Genetic Factors in Nickel Allergy", Journal of Investigative Dermatology, bearing a date of Dec. 2004, pp. xxiv-xxv, vol. 123, No. 6, The Society for Investigative Dermatology, Inc.

(Continued)

*Primary Examiner* — Jerry Lin

(57) ABSTRACT

An apparatus, device, methods, computer program product, and system are described that accept an input defining at least one medical condition; identify within one or more sets of study data at least one agent having a defined level of efficacy in treating the at least one medical condition; identify at least one subpopulation having a defined tolerance for at least one adverse event associated with administration of the at least one agent, the at least one subpopulation exhibiting at least some defined level of efficacy upon administration of the at least one agent to the subpopulation; and present the at least one agent in response to said identification of the at least one subpopulation.

20 Claims, 21 Drawing Sheets

(56) References Cited

OTHER PUBLICATIONS

Bousquet, Jean, et al.; "Factors responsible for differences between asymptomatic subjects and patients presenting and IgE sensitization to allergens"; Allergy; bearing dates of Dec. 2, 2005 and 2006; pp. 671-680; vol. 61; Blackwell Munksgaard.

Bousquet, Jean, et al.; "Epigenetic inheritance of fetal genes in allergic asthma"; Allergy; bearing dates of 2004 and Aug. 13, 2003; pp. 138-147; vol. 59; Blackwell Munksgaard.

Brusic, V., et al.; "Allergen databases"; Allergy; bearing a date of Mar. 26, 2003; pp. 1093-1100; vol. 58; Blackwell Munksgaard.

Burks, A. Wesley; "Recombinant Peanut Allergen Ara h I Expression and IgE Binding in Patients with Peanut Hypersensitivity"; J. Clin. Invest; bearing a date of Oct. 1995; pp. 1715-1721; vol. 96.

Check, Erika, "Genetic expression speaks as loudly as gene type", bearing a date of Jan. 7, 2007, pp. 1-2, nature.com; located at: http://www.nature.com/news/2007/070101/pf/070101-8_pf.html, printed on Jan. 9, 2007.

Cookson, William O.C., "Genetics and Genomics of Chronic Obstructive Pulmonary Disease", Proc Am Thorac Soc, bearing dates of Mar. 16, 2006, Mar. 20, 2006, and Apr. 13, 2006, pp. 473-477, vol. 3.

Couzin, Jennifer, "Human Genetics: In Asians and Whites, Gene Expression Varies by Race", Science, bearing a date of Jan. 12, 2007, pp. 173-174 (abstract pp. 1-3: p. 3 intentionally omitted), vol. 315, No. 5809, located at http://www.sciencemag.org/cgi/content/full/315/5809/173a, printed on Jan. 15, 2007.

D'Ambrosio, Claudio, et al.; "The future of microarray technology: networking the genome search"; Allergy; bearing dates of 2005, and Apr. 20, 2005; pp. 1219-1226; vol. 60; Blackwell Munksgaard.

Dearman, Rebecca J., et al., "Chemical Allergy: Considerations for the Practical Application of Cytokine Profiling", Toxicological Sciences, bearing dates of Sep. 4, 2002, Nov. 11, 2002 and 2003, pp. 137-145, vol. 71, The Society of Toxicology.

Eder, W., et al.; "Association between exposure to farming, allergies and genetic variation in CARD4/NOD1"; Allergy, bearing a date of Sep. 2006; pp. 1117-1124; vol. 61; Issue 9; Blackwell Synergy.

"EU project develops allergy database"; CORDIS; bearing a date of Sep. 14, 2006; p. 1; located at http://cordis.europa.eu/fetch?CALLER=EN_NEWS&ACTION=D; printed on Feb. 16, 2007.

Faux, J.A., et al., "Sensitivity to bee and wasp venoms: association with specific IgE responses to the bee and wasp venom and HLA DRB1 and DPB-1", Clinical & Experimental Allergy, bearing a date of May 1997, pp. 578-583 (abstract pp. 1-2), vol. 27, No. 5, Blackwell Publishing.

Frederickson, Robert M., "Lab Automation & Robotics: Sample management instrumentation and software in the high-throughput laboratory", Cambridge Healthtech Institute, bearing a date of Oct. 26, 2006, pp. 1-4, Bio-IT World, Inc., Needham, MA.

Harle, D.G., et al., "Detection of thiopentone-reactive IgE antibodies following anaphylactoid reactions during anaesthesia", Clin Allergy, bearing a date of Sep. 1986, pp. 493-498; vol. 16, No. 5.

Immervoll, Thomas and Wjst, Matthias; "Current status of the Asthma and Allergy Database"; Nucleic Acids Research, bearing a date of 1999; pp. 213-214; vol. 27, No. 1; Oxford University Press.

Ivanciuc, Ovidiu, et al.; "Data mining of sequences and 3D structures of allergenic proteins"; Bioinformatics; bearing dates of Jan. 17, 2002; Mar. 26, 2002; and Apr. 28, 2002; pp. 1358-1364; vol. 18; No. 10.

"Journal of Allergy and Clinical Immunology Says Peanut Allergy May Have Genetic Link", bearing a date of Jul. 17, 2000, pp. 1-2, PR Newswire.

Kalayci, O., et al.; "ALOX5 promoter genotype, asthma severity and $LTC_4$ production by eosinophils"; Allergy; bearing dates of Aug. 2, 2005 and 2006; pp. 97-103; vol. 61; Blackwell Munksgaard.

Kim, Jeong Joong PhD; et al.; "Chemokine RANTES Promoter Polymorphisms in Allergic Rhinitis"; The Laryngoscope; bearing a date of Apr. 2004; pp. 666-669; vol. 114; Issue 4.

Kjellman, N.I., et al., "Cord blood IgE determination for allergy prediction—a follow-up to seven years of age in 1651 children", Annals of Allergy, bearing a date of Aug. 1984, pp. 167-171; vol. 53, No. 2.

Levine, Bruce L., et al., "Gene transfer in humans using a conditionally replicating lentiviral vector", Proceedings of the National Academy of Sciences of the United States of America (PNAS), bearing a date of Nov. 14, 2006, pp. 17372-17377, vol. 103, No. 46, located at www.pnas.org/cgi/doi/10.1073/pnas.0608138103.

"List of Allergens"; bearing a date of Feb. 20, 2007; located at http://www.allergen.org/Allergen.aspx; (Upon the Examiner's request, a printed copy of this data base can be supplied).

Moffatt, Miriam F., et al., "Atopy, respiratory function and HLA-DR in Aboriginal Australians", Human Molecular Genetics, bearing dates of Nov. 4, 2002 and Jan. 9, 2003, pp. 625-630, vol. 12, No. 6, Oxford University Press.

Moore, W.C., et al.; "Characterization of the severe asthma phenotype by the National Heart, Lung and Blood Institute's Severe Asthma Research Program"; J Allergy Clin Immunol.; bearing a date of Feb. 2007; pp. 405-413; vol. 119; No. 2.

Nicholson, Jeremy K., "Global systems biology, personalized medicine and molecular epidemiology", Molecular Systems Biology, bearing a date of Oct. 3, 2006, Article No. 52, pp. 1-6, EMBO & Nature Publishing Group.

Ono, S.J., "Molecular genetics of allergic diseases", Annu Rev Immunol, bearing a date of 2000, pp. 347-366; vol. 18.

Raloff, J., "Peanut allergy found common and increasing", Science News, bearing a date of Sep. 7, 1996, vol. 150, No. 10, p. 150; Science Service.

Rieger-Ziegler, Verena, et al., "Hymenoptera Venom Allergy: Time Course of Specific IgE Concentrations during the first Weeks after a Sting", International Archives of Allergy and Immunology, bearing dates of 1999, Nov. 19, 1998, Jun. 23, 1999, and 2006, pp. 166-168, vol. 120.

Rufo, Paul A. MD, MMSC, "Study to Identify Non-Invasive Markers of Gastrointestinal Allergy", ClinicalTrials.gov, bearing a date of Jan. 4, 2006, pp. 1-4, located at http://www.clinicaltrials.gov/ct/gui/show/NCT00272818, printed on Jan. 24, 2007.

Sheikh, Aziz, MRCP, MRCGP, "Itch, sneeze and wheeze: the genetics of atopic allergy", Journal of the Royal Society of Medicine, bearing a date of Jan. 2002, pp. 14-17, vol. 95, London, England.

Sicherer, Scott H., MD, "Determinants of systemic manifestations of food allergy", J Allergy Clin Immunol, bearing a date of 2000, pp. S251-S257, vol. 106, No. 5, Mosby, Inc.

Spielman, Richard S., et al.; "Common genetic variants account for differences in gene expression among ethnic groups"; Nature Genetics; bearing a date of Jan. 7, 2007; pp. 226-231; vol. 39.

Szalai, Csaba Ph.D, et al., "Polymorphism in the gene regulatory region of MCP-1 is associated with asthma susceptibility and severity"; J Allergy Clin Immunol.; bearing a date of Sep. 2001; pp. 375-381; vol. 108; Issue 3.

Tarkan, Laurie, "In Testing for Allergies, a Single Shot May Suffice"; The New York Times, bearing a date of Mar. 20, 2007; pp. 1-3; New York, NY.

Vandebriel, R.J., et al., "Gene polymorphisms within the immune system that may underlie drug allergy", Naunyn Schmiedebergs Arch Pharmacol, bearing dates of Oct. 3, 2003 and Jan. 2004, pp. 125-132, vol. 369, No. 1, printed on Jan. 29, 2007.

Vennekens, Rudi, et al.; "Increased IgE-dependent mast cell activation and anaphylactic responses in mice lacking the calcium-activated nonselective cation channel $TRPM_4$"; Nature Immunology; bearing a date of Feb. 11, 2007, pp. 312-320; vol. 8.

Vercelli, Donata, MD; "The functional genomics of CD14 and its role in IgE responses: An integrated view"; Journal of Allergy and Clinical Immunology; bearing a date of Jan. 2002; pp. 14-21; vol. 109; Issue 1.

Werner, M., et al.; "Asthma is associated with single-nucleotide polymorphisms in ADAM33"; Clinical & Experimental Allergy; bearing a date of Jan. 2004; pp. 26-31; vol. 34, Issue 1; Blackwell Synergy.

(56) References Cited

OTHER PUBLICATIONS

Wjst, Matthias and Immervoll, Thomas; "An Internet linkage and mutation database for the complex phenotype asthma"; Bioinformatics; bearing a date of Oct. 1998; pp. 827-828; vol. 14; No. 9.
Yang, Jing, et al., "HLA-DRB genotype and specific IgE responses in patients with allergies to penicillins", Chin, Med J, bearing dates of Aug. 26, 2005 and 2006, pp. 458-466, vol. 119, No. 6.
Ziegler, V., et al., "INPRET—database on predictive tests (allergy)"; Seminars in Dermatology.; bearing a date of Jun. 1989; pp. 80-82; vol. 8, No. 2.
U.S. Appl. No. 11/893,612, Jung et al.
U.S. Appl. No. 11/893,370, Jung et al.
U.S. Appl. No. 11/893,106, Jung et al.
U.S. Appl. No. 11/891,669, Jung et al.
U.S. Appl. No. 11/881,803, Jung et al.
U.S. Appl. No. 11/881,802, Jung et al.
U.S. Appl. No. 11/821,537, Jung et al.
U.S. Appl. No. 11/821,105, Jung et al.
U.S. Appl. No. 11/810,358, Jung et al.
U.S. Appl. No. 11/809,776, Jung et al.
U.S. Appl. No. 11/728,311, Jung et al.
U.S. Appl. No. 11/728,026, Jung et al.
U.S. Appl. No. 11/728,025, Jung et al.
Adjei, AA; "Pemetrexed (ALIMTA), a novel multitargeted antineoplastic agent"; Clin Cancer Res.; bearing a date of Jun. 15, 2004; pp. 4276s-4280s (abstract p. 1); vol. 10, No. 12, Pt 2; PubMed; located at http://www.ncbi.nlm.nih.gov/entrez/query.fcgi?db=pubmed&cmd=R; printed on Jul. 31, 2006.
Amouzou, Emile K., et al., "High prevalence of hyperhomocysteinemia related to folate deficiency and the 677C → T mutation of the gene encoding methylenetetrahydrofolate reductase in coastal West Africa[1-3]", American Journal of Clinical Nutrition, bearing a date of 2004; pp. 619-624; vol. 79; American Society for Clinical Nutrition; printed on Jul. 31, 2006.
Bagga, Sandeep Kumar, "Multi-center clinical trial connectivity, express data management and SAS programming", bearing dates of Mar. 11, 2002 and Aug. 4, 2006; pp. 1-2; PHARMABIZ.com; located at http://www.phamabiz.com/article/detnews.asp?articleid=11396&se; printed on Aug. 3, 2006.
Calvert, AH; "Biochemical pharmacology of pemetrexed"; Oncology; bearing a date of Nov. 2004; pp. 13-17 (abstract p. 1); vol. 18, No. 13 Suppl 8; PubMed; located at http://www.ncbi.nlm.nih.gov/entrez/query.fcgi?db=pubmed&cmd=R; printed on Jul. 31, 2006.
Calvert, A. H., et al., "Clinical studies with MTA", Br J Cancer, bearing a date of 1998; pp. 35-40 (abstract, p. 1); vol. 78; Suppl 3; PubMed; located at http://www.ncbi.nlm.nih.gov/entrez/query.fcgi?db=pubmed&cmd=R . . . , printed on Jul. 31, 2006.
Calvert, H.; "Folate Status and the safety profile of antifolates"; Semin Oncol., bearing a date of Apr. 2002; pp. 3-7 (abstract p. 1); vol. 29; No. 2 Suppl 5; PubMed; located at http://www.ncbi.nlm.nih.gov/entrez/query.fcgi?db=pubmed&cmd=R; printed on Jul. 31, 2006.
Carmel, Ralph, et al.; "Serum cobalamin, homocysteine, and methylmalonic acid concentrations in a multiethnic elderly population: ethnic and sex differences in cobalamin and metabolite abnormalities 1-3"; Am J Clin Nutr; bearing a date of 1999; pp. 904-910; vol. 70; American Society of Clinical Nutrition; printed on Jul. 31, 2006.
Cascorbi, I.; "Pharmacogenetics of cytochrome p4502D6: genetic background and clinical implication"; Eur J Clin Invest.; bearing dates of Nov. 2003 and Jun. 6, 2006; pp. 17-22 (abstract p. 1); vol. 33, Suppl 2; PubMed; located at http://www.ncbi.nlm,nih.gov/entrez/query.fcgi?CMD=displayfilter; printed on Jun. 13, 2006.
Chiacchierini, Richard P.; "Clinical Trials—Biostatistics and the Analysis of Clinical Data"; bearing a date of 2005; pp. 1-8; Medical Device Link; located at http://devicelink.com/grabber.php3?URL=http://devicelink.com; printed on Aug. 3, 2006.
Cook, David I., et al., "Subgroup Analysis in Clinical Trials"; Medical Journal of Australia; bearing dates of Feb. 9, 2004 and 2004; pp. 289-291 (pp. 1-9 from website); vol. 180, No. 6; located at http://www.mja.com.au/public/issues/180_06_150304/coo10086_fm.html; printed on Jul. 20, 2006.

Dreifus, Claudia, "A Conversation with Mary V. Relling: Saving Lives with Tailor-Made Medication"; bearing a date of Aug. 29, 2006; pp. 1-3; New York Times; located at http://www.nytimes.com/2006/08/29/health/29conv.html?pagewant, printed on Aug. 29, 2006.
Eismann, U, et al.; "Pemetrexed: mRNA expression of the target genes TS, GARFT and DHFR correlates with the in vitro chemosensitivity of human solid tumors"; Int J Clin Pharmacol Ther.; bearing a date of Dec. 2005; pp. 567-569 (abstract p. 1); vol. 43, No. 12; PubMed; located at http://www.ncbi.nlm.nih.gov/entrez/query.fcgi?db=pubmed&cmd=R; printed on Jul. 31, 2006.
Gheuens, Jan; Edwards, Carl; "Pharmocagenomics and Pharmaceutical Research, Development and Therapy"; "Pharmacogenomics and Molecular Medicine in Application to Rheumatoid Arthritis"; bearing the dates of Feb. 12, 2001 and Feb. 13, 2001; pp. 1-4; National Institute of Statistical Sciences, located at http://www.niss.org/affiliates/genworkshop200102/abstracts.html; printed on Jul. 20, 2006.
"Guidance for Industry: Pharmocogenomic Data Submissions"; bearing a date of Mar. 31, 2005; pp. 1-22; U.S. Food & Drug Administration; located at http://www.fda.gov/CbER/gdlns/pharmdtasub.htm, printed on Jul. 20, 2006.
Hanauske, Axel-R., et al., "Pemetrexed Disodium: A Novel Antifolate Clinically Active Against Multiple Solid Tumors", The Oncologist, bearing dates of Jan. 15, 2001 and May 22, 2001; pp. 363-373; vol. 6.
"HelixTree® Genetics Analysis Software for Mac OS X"; bearing dates of 2001 and 2006; pp. 1-16; Golden Helix; located at http://www.goldenhelix.com/HelixTree_MacOSX_details.html, printed on Sep. 19, 2006.
John W., et al., "Activity of multitargeted antifolate (pemetrexed disodium, LY231514) in patients with advanced colorectal carcinoma: results from a phase II study", Cancer; bearing a date of Apr. 15, 2000; pp. 1807-1813; (abstract p. 1) vol. 88; No. 8; PubMed; located at http://www.ncbi.nlm.nih.gov/entrez/query.fcgi?db=pubmed&cmd=R, printed on Jul. 31, 2006.
Johnson, Carolyn; "Should Medicine Be Colorblind?"; bearing a date of Aug. 24, 2004; pp. 1-2; The Boston Globe; located at http://222.boston.com/news/globe/health_science/articles/2004/08; printed on Jun. 7, 2006.
Lai, EC, "Micro RNAs are complementary to 3' UTR sequence motifs that mediate negative post-transcriptional regulation"; Nat Genet.; bearing a date of Apr. 2002; pp. 363-364 (abstract p. 1); vol. 30, No. 4; PubMed; located at http://www.ncbi.nlm.nih.gov/entrez/query.fcgi?db=pubmed&cmd=Retrieve&db=; printed on Aug. 14, 2006.
Lamba, Vishal, et al.; Hepatic CYP2B6 Expression: Gender and Ethnic Differences and Relationship to CYP2B6 Genotype and CAR (Constitutive Androstane Receptor) Expression; The Journal of Pharmacology and Experimental Therapeutics; bearing dates of May 21, 2003 and Aug. 22, 2003; pp. 906-922; vol. 307, No. 3.
Latz, J. E., et al., "A semimechanistic-physiologic population pharmacokinetic/pharmacodynamic model for neutropenia following pemetrexed therapy", Cancer Chemother Pharmacol., bearing a date of Apr. 2006; pp. 412-426; vol. 57; No. 4; (Abstract bearing a date of Dec. 2, 2005, pp. 1-2); located at http://www.ncbi.nlm.nih.gov/entrez/query.fcgi?db=pubmed&cmd=R; printed on Jul. 31, 2006.
Latz, J. E., et al., "A semimechanistic-physiologic population pharmacokinetic/pharmacodynamic model for neutropenia following pemetrexed therapy", Cancer Chemother Pharmacol., bearing dates of Dec. 21, 2004, Apr. 17, 2005, Dec. 2, 2005 and Apr. 2006; pp. 412-426; vol. 57; No. 4; Springer-Verlag.
Latz, JE, et al.; "Clinical application of a semimechanistic-physiologic population PK/PD model for neutropenia following pemetrexed therapy"; Cancer Chemother Pharmacol.; bearing a date of Apr. 2006; pp. 427-435 (abstract p. 1); vol. 57, No. 4; PubMed; located at http://www.ncbi.nlmnih.gov/entrez/query.fcgi?db=pubmed&cmd=R; printed on Jul. 31, 2006.
Latz, J. E. et al, "Population pharmacokinetic analysis of ten phase II clinical trials of pemetrexed in cancer patients", Cancer Chemother Pharmacol., bearing a date of Apr. 2006; pp. 401-411; vol. 57; No. 4; (Abstract bearing a date of Dec. 2, 2005, pp. 1-2); located at http://www.ncbi.nlm.nih.gov/entrez/query.fcgi?db=pubmed&cmd=R; printed on Jul. 31, 2006.

(56) References Cited

OTHER PUBLICATIONS

Latz, Jane E. et al, "Population pharmacokinetic analysis of ten phase II clinical trials of pemetrexed in cancer patients", Cancer Chemother Pharmacol.; bearing dates of Dec. 22, 2004, Apr. 17, 2005, Dec. 2, 2005 and 2005; pp. 401-411; vol. 57; Springer-Verlag.
Manegold., C, et al.; "Front-line treatment of advanced non-small-cell lung cancer with MTA (LY231514, pemetrexed disodium, ALIMTA) and cisplatin: a multicenter phase II trial"; Ann Oncol; bearing a date of Apr. 2000; pp. 435-440 (abstract p. 1); vol. 11, No. 4; PubMed located at http://222.ncbi.nlm.nih.gov/entrez/query.fcgi?db=pubmed&cmd=R; printed on Jul. 31, 2001.
"Markers of Gene, Protein, or Micro-RNA Activity Predict Outcome in Prostate and Colorectal Cancers"; bearing a date of Apr. 8, 2006; pp. 1-3; Science Daily; located at http://sciencedaily.com/releases/2006/04/060407143815.htm; printed on Aug. 14, 2006.
Mazieres J; "Wnt2 as a new therapeutic target in malignant pleural mesothelioma"; Int J Cancer, bearing a date of Nov. 1, 2005; pp. 326-332 (abstract p. 1); vol. 117, No. 2; PubMed; located at http://www.ncbi.nlm.nih.gov/entrez/query.fcgi?db=pubmed&cmd=R; printed on Jul. 31, 2006.
Mcdonald, AC, et al.; "A phase I and pharmacokinetic study of LY231514, the multitargeted antifolate"; Clin Cancer Res.; bearing a date of Mar. 1998; pp. 605-610 (abstract p. 1) vol. 4; No. 3; PubMed; located at http://www.ncbi.nlm.nih.gov/entrez/query.fcgi?db=pubmed&cmd=R; printed on Jul. 31, 2006.
Mcdowell, Sarah E., et al.; "Systematic review and meta-analysis of ethnic differences in risks of adverse reactions to drugs used in cardiovascular medicine"; bearing dates of 2001-2006; (abstract p. 1); PharmGKB; located at http://www.pharmgkb.org/do/serve?objId=PA144559843 printed on Aug. 18, 2006.
Mcdowell, Sarah E., et al.; "Systematic review and meta-analysis of ethnic differences in risks of adverse reactions to drugs in cardiovascular medicine"; bearing dates of Feb. 23, 2006, May 20, 2006 and May 5, 2006; pp. 1177-1181 (pp. 1-14 from website); located at http://bmj.bmjjournals.com/cgi/content/full/332/7551/1177; printed on Aug. 22, 2006.
Minematsu, N. et al., "Limitation of cigarette consumption by CYP2A6*4, *7 and *9 polymorphisms", Eur Respir Journal, 2006; pp. 289-292 (abstract p. 1); vol. 27; ERS Journals Ltd.; printed on Jun. 19, 2006.
Nainggolan, Lisa, First genetically targeted drug for heart disease?, bearing a date of Jul. 11, 2006; pp. 1-4.
"New Data on Lung Cancer Trials with Targetn® is Presented at ASCO"; bearing a date of Jun. 5, 2006; pp. 1-3; Ligand Pharmaceutical Incorporated.
Niyikiza, Clet, et al.; "Homocysteine and Methylmalonic Acid: Markers to Predict and Avoid Toxicity from Pemetrexed Therapy"; Mol Cancer Ther., bearing a date of May 2002, pp. 545-552 (abstract p. 1); vol. 1, PubMed; located at http://www.ncbi.nlm.nih.gov/entrez/query.fcgi?db=pubmed&cmd=R; printed on Jul. 31, 2006.
Niyikiza, Clet, et al.; "Homocysteine and Methylmalonic Acid: Markers to Predict and Avoid Toxicity from Pemetrexed Therapy"; Molecular Cancer Therapeutics, May 2002, pp. 545-552; vol. 1.
O'Dwyer, P. J., et al., "Overview of phase II trails of MTA in solid tumors", Semin Oncol., bearing a date Apr. 1999; pp. 99-104; (abstract p. 1) vol. 26; No. 2; Suppl 6; PubMed; located at http://www.ncbi.nlm.nih.gov/entrez/query.fcgi?db=pubmed&cmd=R, printed on Jul. 31, 2006.
O'Kane, Dennis J. et al., "Pharmacogenomics and Reducing the Frequency of Adverse Drug Events", Pharmacogenomics, bearing a date of 2003, pp. 1-4; vol. 4, No. 1; Ashley Publications Ltd.
Otey, Matthew E., et al., "Dissimilarity Measures for Detecting Hepatotoxicity in Clinical Trial Data", 2006 SIAM Conference on Data Mining, bearing dates of Apr. 20, 2006 and Apr. 22, 2006; pp. 1-7; located at http://www.siam.org/meetings/sdm06/proceedings/05oteym.pdf., printed on Jul. 20, 2006.
Ouellet, D., et al.; "Population pharmacokinetics of pemetrexed disodium (ALIMTA) I in patients with cancer"; Cancer Chemother Pharmacol.; bearing a date of 2000, pp. 227-234 (abstract p. 1); vol. 46, No. 3; PubMed; located at http://www.ncbi.nlm.nih.gov/entrez/query.fcgi?db=pubmed&cmd=R; printed on Jul. 31, 2006.
"Pharmacogenetics as a Predictor of Toxicity in Pre-Menopausal Women Receiving Doxorubicin and Cyclophosphamide in Early Breast Cancer", bearing dates of Jan. 2006 and Jul. 13, 2006; pp. 1-3; Clinical Trials.gov, located at http://www.clinicaltrials.gov/ct/show/NCT00352872jsessionid=F1; printed on Aug. 17, 2006.
Rogatko, A. et al., "Patient characteristics compete with dose as predictors of acute treatment toxicity in early phase clinical trials", Clinical Cancer Research, Jul. 15, 2004; pp. 4645-4651 (pp. 1-14 from website); vol. 10; American Association of Cancer Research.
Rollins, KD, et al.; "Pemetrexed: a multitargeted antifolate"; Clin Ther.; bearing a date of Sep. 2005; pp. 1343-1382 (abstract pp. 1-2); vol. 27, No. 9, PubMed; located at http://www.ncbi.nlm.nih.gov/entrez/query.fcgi?db=pubmed&cmd=R; printed on Jul. 31, 2006.
Salamone, Salvatore, "Pfizer Data Mining Focuses on Clinical Trials"; bearing a date of Feb. 23, 2006; pp. 1-2; Bio-IT World.
Scagliotti, GV;; et al.; "Phase II study of pemetrexed with and without folic acid and vitamin B 12 as front-line therapy in malignant pleural mesothelioma"; J Clin Oncol.; bearing a date of Apr. 15, 2003; pp. 1556-1561; (abstract p. 1); vol. 21, No. 8; PubMed; located at http://www.ncbi.nlm.nih.gov/entrez/query.fcgi?db=pubmed&cmd=R; printed on Jul. 31, 2006.
Sharp, Linda; Little, Julian; "Polymorphisms in Genes Involved in Folate Metabolism and Colorectal Neoplasia: A HuGE Review"; bearing a date of Mar. 1, 2004; pp. 1-13; National Office of Public Health Genomics; located at http://www.cdc.gov/genomics/hugenet/reviews/neoplasia.htm#refer; printed on Aug. 1, 2006.
Sigmond, J., et al.; "Induction of resistance to the multitargeted antifolate Pemetrexed (ALIMTA) in WiDr human colon cancer cells is associated with thymidylate synthase overexpression"; Biochem Pharmacol; bearing a date of Aug. 1, 2003; pp. 431-438 (abstract p. 1); vol. 66, No. 3; PubMed; located at http://www.ncbi.nlm.nih.gov/entrez/query.fcgi?db=pubmed&cmd=R; printed on Jul. 31, 2006.
"Technique Offers New View of Dynamic Biological Landscape"; bearing a date of Nov. 4, 2005; pp. 1-3; Howard Hughes Medical Institute.
Van Noorden, Richard; "Another source of genetic variability mapped: Researchers chart out insertions and deletions in the genome"; pp. 1-2; bearing a date of Aug. 10, 2006; news@nature.com; located at http://www.nature.com/news/2006/060807/pf/060807-15_pf.html; printed on Aug. 11, 2006.
Vogelzang, Nicholas J., et al., "Phase III Study of Pemetrexed in Combination with Cisplatin Verus Cisplatin Alone in Patients with Malignant Pleural Mesothelioma"; Journal of Clinical Oncology, bearing a date of Jul. 15, 2003; pp. 2636-2644; vol. 21, No. 14; American Society of Clinical Oncology; printed on Aug. 1, 2006.
Wilson, James F., et al., "Population Genetic Structure of Variable Drug Response", Nature Genetics, bearing a date of Oct. 29, 2001; pp. 265-269; vol. 29; Nature Publishing Group; located at www.nature.com/ng/journal/v29/n3/full/ng761.html, printed on Aug. 18, 2006.
Worzalla, J. F., Schultz, RM; "Role of folic acid in modulating the toxicity and efficacy of the multitargeted antifolate, LY231514", Anticancer Res., bearing dates of Sep.-Oct. 1998; pp. 3235-3239; (abstract p. 1) vol. 18; No. 5A; PubMed; located at http://www.ncbi.nlm.nih.gov/entrez/query.fcgi?db=pubmed&cmd=R.; printed on Jul. 31, 2006.
Zhao, R., et al.; "Loss of reduced folate carrier function and folate depletion result in enhanced pemetrexed inhibition of purine synthesis"; Clin Cancer Res.; bearing a date of Feb. 1, 2005; pp. 1294-1301 (abstract p. 1); vol. 11, No. 3; located at http://www.ncbi.nlm.nih.gov/entrez/query.fcgi?db=pubmed&cmd=R; printed on Jul. 31, 2006.
Dehais, Patrice et al.; "An Interactive System for Database in Immunogenetics"; Proceedings of the Twenty-Seventh Annual Hawaii International Conference on System Sciences; Jan. 4-7, 1994; pp. 25-34; vol. 5; IEEE; Maui, Hawaii.
Sicherer, Scott H.; "Food allergy"; The Lancet; bearing a date of Aug. 31, 2002; pp. 701-710; vol. 360;The Lancet Publishing Group.
Tomita et al.; "Artificial neural network approach for selection of susceptible single nucleotide polymorphisms and construction of prediction model on childhood allergic asthma"; BMC Bioinformatics; Sep. 1, 2004; pp. 1-13; vol. 5, Issue 120; BioMed Central Ltd.

(56) References Cited

OTHER PUBLICATIONS

Qiao et al.; "Specific Serum IgE Levels and FcεRIβ Genetic Polymorphism in Patients with Penicillins Allergy"; Allergy; accepted for publication Mar. 31, 2004; pp. 1326-1332; vol. 59; Blackwell Munksgaard.

Blumenthal et al.; "A genome-wide search for allergic response (atopy) genes in three ethnic groups: Collaborative Study on the Genetics of Asthma"; Human Genetics; bearing a date of Oct. 25, 2003; pp. 157-164; vol. 114; Springer-Verlag.

* cited by examiner

FIG. 5

| | 306 Study Efficacy Data | 308 Study Adverse Event Data | 310 Subpopulation Efficacy Data | 312 Subpopulation Adverse Event Data | 314 Subpopulation Identifier Data |
|---|---|---|---|---|---|
| Pemetrexed (Alimta) ← 502 | Acceptable efficacy | Odds ratio of developing severe toxicity = 1 | Efficacy maintained or improved | Methylmalonic acid levels < 119.0 nmol/l (Odds ratio of developing severe toxicity = 0.3) | Supplementation with folic acid and vitamin B12 to decrease methylmalonic acid levels |
| Pemetrexed (Alimta) ← 504 | Acceptable efficacy | Odds ratio of developing severe toxicity = 1 | Efficacy maintained or improved | Total homocysteine levels < 7.5 µmol/l (Odds ratio of developing severe toxicity = 0.7) | Supplementation with folic acid and/or vitamin B12 to decrease total homocysteine levels |

FIG. 6

| | 306 Study Efficacy Data | 308 Study Adverse Event Data | 310 Subpopulation Efficacy Data | 312 Subpopulation Adverse Event Data | 314 Subpopulation Identifier Data |
|---|---|---|---|---|---|
| Pemetrexed (Alimta) [602] | 41.3% partial response rate for Pemetrexed /Cisplatin vs. 16.7% for Cisplatin alone | 41.4% Grade 3/4 Neutropenia (partial and never supplemented group) | 45.6% partial response rate for Pemetrexed /Cisplatin vs. 19.0% for Cisplatin alone | 23.2% Grade 3/4 Neutropenia (full supplementation group) | Supplementation with folic acid and vitamin B12 |
| Pemetrexed (Alimta) [604] | 41.3% partial response rate for Pemetrexed /Cisplatin vs. 16.7% for Cisplatin alone | 31.3% Nausea (never supplemented group) | 45.6% partial response rate for Pemetrexed /Cisplatin vs. 19.0% for Cisplatin alone | 11.9% Nausea (full and partial supplementation group) | Supplementation with folic acid and vitamin B12 |
| Pemetrexed (Alimta) [606] | 41.3% partial response rate for Pemetrexed /Cisplatin vs. 16.7% for Cisplatin alone | 31.3% Vomiting (never supplemented group) | 45.6% partial response rate for Pemetrexed /Cisplatin vs. 19.0% for Cisplatin alone | 10.3% Vomiting (full and partial supplementation group) | Supplementation with folic acid and vitamin B12 |

FIG. 7

| | 306 Study Efficacy Data | 308 Study Adverse Event Data | 310 Subpopulation Efficacy Data | 312 Subpopulation Adverse Event Data | 314 Subpopulation Identifier Data |
|---|---|---|---|---|---|
| Ifosfamide | Acceptable efficacy | Darkened and thickened skin | Maintained efficacy | Decreased incidence of darkened and thickened skin in individuals with a specific CYP2B6 SNP profile | Increased activity of CYP2B6 in Hispanic females aged 20-45 |
| ACE Inhibitor | Acceptable efficacy | Angio-edema (Relative risk = 1) | Acceptable efficacy | Increased incidence of angio-edema in Black patients (Relative risk = 3) | Black patients of West Indian descent |

702 → (Ifosfamide row)
704 → (ACE Inhibitor row)

FIG. 16A

Key To FIG. 16: | 16A | 16B |

Start → accepting an input defining at least one medical condition (810)

↓ identifying within one or more sets of study data at least one database having data corresponding to the one or more sets of study data at least one agent having a defined level of efficacy in treating the at least one medical condition (820)

(A)

1402 searching at least one database having data corresponding to the one or more sets of study data; and extracting the at least one subpopulation having a defined tolerance for at least one adverse event associated with administration of the at least one agent from the at least one database in response to said searching

- 1602 extracting from the at least one database a subpopulation characterized by one or more genetic parameters
- 1604 extracting from the at least one database a subpopulation characterized by one or more epigenetic parameters
- 1606 extracting from the at least one database a subpopulation characterized by one or more bio-chemical parameters
- 1608 extracting from the at least one database a subpopulation characterized by one or more gene expression parameters
- 1610 extracting from the at least one database a subpopulation characterized by one or more protein expression parameters
- 1612 extracting from the at least one database a subpopulation characterized by one or more behavioral parameters (B)

↓ presenting the at least one agent in response to said identifying at least one subpopulation (830)

→ End (840)

FIG. 16B

| 16A | 16B |
| Key To |
| FIG. 16 |

1402 searching at least one database having data corresponding to the one or more sets of study data; and extracting the at least one subpopulation having a defined tolerance for at least one adverse event associated with administration of the at least one agent from the at least one database in response to said searching 1614 extracting from the at least one database a subpopulation characterized by one or more physiologic parameters 1616 extracting from the at least one database a subpopulation characterized by one or more demographic parameters 1617 extracting from the at least one database a subpopulation characterized by one or more of age, gender, ethnicity, race, liver enzyme genotype, or medical history 1618 extracting from the at least one database a subpopulation characterized by one or more of lifestyle, exercise regimen, diet, nutritional regimen, dietary supplementation, concomitant medical therapy, or concomitant alternative medical therapy 1620 extracting from the at least one database a subpopulation characterized by one or more of linkage disequilibrium analysis profile, haplotype profile, single nucleotide polymorphism profile, or individual genetic sequence profile 1622 extracting from the at least one database a subpopulation having a significantly lower incidence of at least one adverse event than that of at least one reported clinical trial for the at least one agent

830

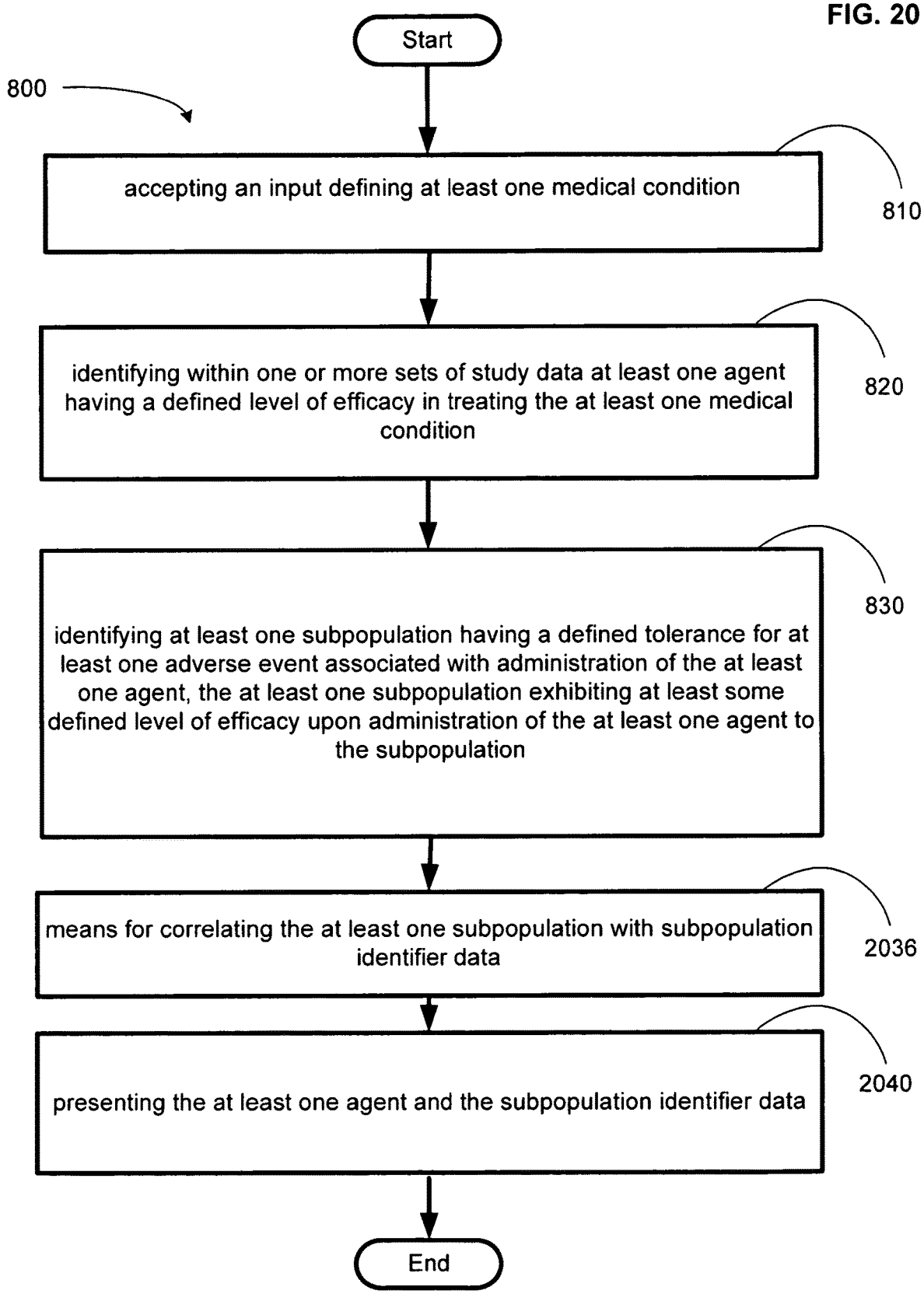

COMPUTATIONAL SYSTEMS FOR BIOMEDICAL DATA

TECHNICAL FIELD

This description relates to data handling techniques.

SUMMARY

An embodiment provides a method. In one implementation, the method includes but is not limited to accepting an input defining at least one medical condition, identifying within one or more sets of study data at least one agent having a defined level of efficacy in treating the at least one medical condition, identifying at least one subpopulation having a defined tolerance for at least one adverse event associated with administration of the at least one agent, the at least one subpopulation exhibiting at least some defined level of efficacy upon administration of the at least one agent to the subpopulation, and presenting the at least one agent in response to said identifying at least one subpopulation. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

An embodiment provides a method. In one implementation, the method includes but is not limited to accepting an input defining at least one treatment goal, identifying within one or more sets of study data at least one agent having a defined level of efficacy in addressing the at least one treatment goal, identifying at least one subpopulation having a defined tolerance for at least one adverse event associated with administration of the at least one agent, the at least one subpopulation exhibiting at least some defined level of efficacy upon administration of the at least one agent to the subpopulation, and presenting the at least one in response to said identifying at least one population. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

In addition to the foregoing, various other embodiments are set forth and described in the text (e.g., claims and/or detailed description) and/or drawings of the present description.

The foregoing is a summary and thus contains, by necessity, simplifications, generalizations and omissions of detail; consequently, those skilled in the art will appreciate that the summary is illustrative only and is not intended to be in any way limiting. Other aspects, features, and advantages of the devices and/or processes described herein, as defined by the claims, will become apparent in the detailed description set forth herein.

BRIEF DESCRIPTION OF THE DRAWINGS

FIG. 5 illustrates another alternative embodiment of study data associated with the data analysis system of FIG. 1, with specific examples of study data.

FIG. 6 illustrates additional alternative embodiments of study data associated with the data analysis system of FIG. 1, with specific examples of study data.

FIG. 7 illustrates additional alternative embodiments of study data associated with the data analysis system of FIG. 1, with specific examples of study data.

FIG. 16 illustrates an alternative embodiment of the example operational flow of FIG. 8.

FIG. 20 illustrates another operational flow representing example operations related to medical adverse event data systems.

The use of the same symbols in different drawings typically indicates similar or identical items.

DETAILED DESCRIPTION

Figure 1:
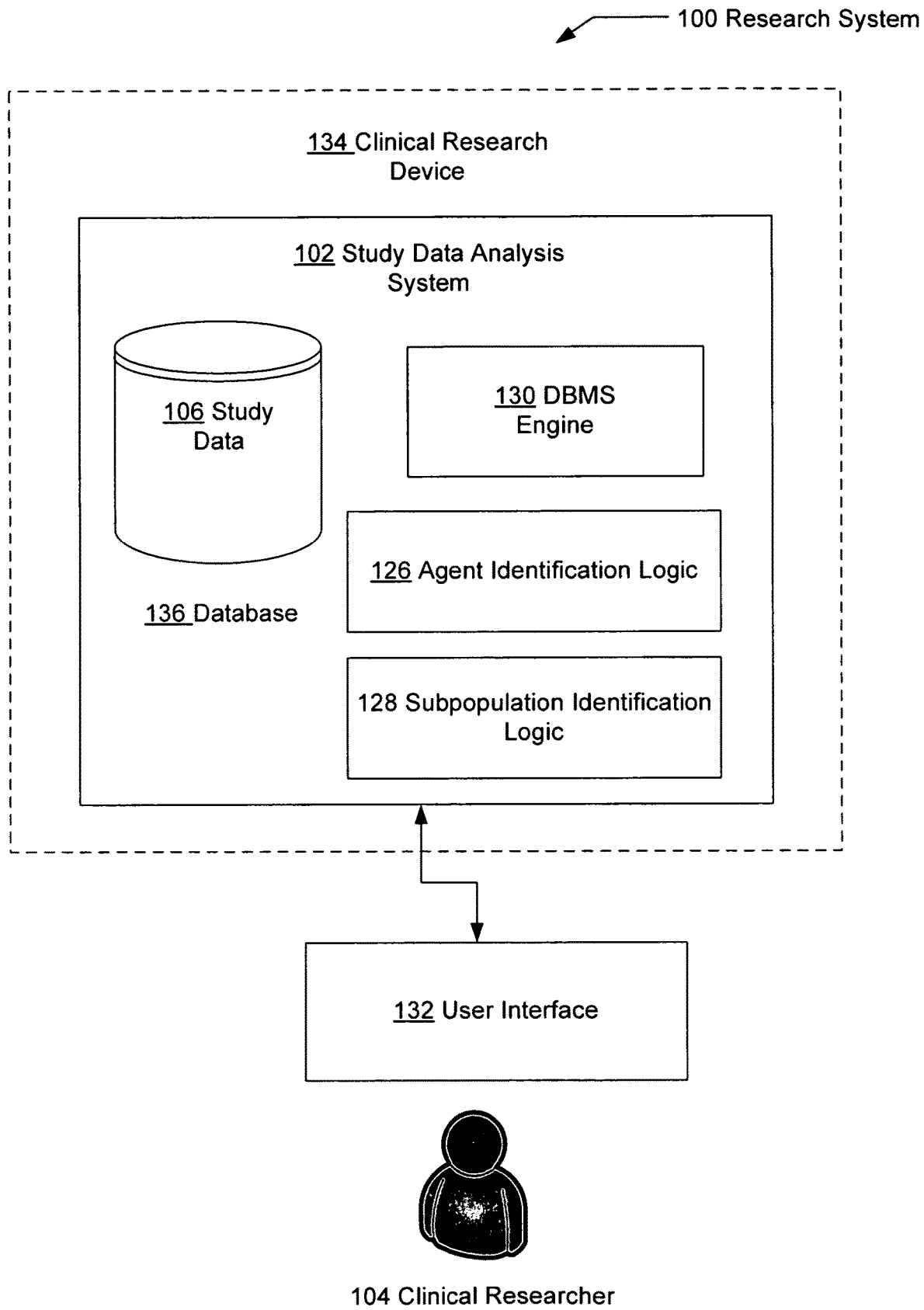
FIG. 1 illustrates an example data analysis system in which embodiments may be implemented, perhaps in a device.

FIG. 1 illustrates an example research system 100 in which embodiments may be implemented. The research system 100 includes a study data analysis system 102. The study data analysis system 102 may be used, for example, to store, recall, access, implement, or otherwise use information obtained from study data 106.

The study data analysis system 102 may be used, for example, to identify agent(s) associated with one or more medical conditions which are associated with a specific subpopulation(s) of individuals for whom the incidence of one or more adverse events is acceptable at a defined level. The study data analysis system 102 may identify such agent(s) by, for example, storing, analyzing and/or providing information obtained from study data 106 as to the safety and effectiveness of the agent(s). An adverse event, also known as an adverse effect, side effect, or complication, is typically a consequence of agent administration other than the intended consequence of agent administration. An agent, as used herein, can be, for example, a medical or non-medical intervention, including, for example, administration of prescription or non-prescription medications, small molecules or biologics, nutraceuticals, or dietary supplements. An agent may also be, for example, alcohol or an illicit substance. A medical condition, as used herein, can be, for example, a treatment goal or disorder meriting clinical or alternative medical intervention. Medical conditions may also be voluntary procedures, for example, cosmetic procedures. Treatment, as used herein, can refer to treating and/or prevention.

As a further example, the study data analysis system 102 can provide information about which agent(s) are candidates for further testing and development according to defined efficacy levels and defined levels of tolerance for one or more adverse events. On the basis of study data analysis, for example, for a given condition, an agent may be identified that will be effective in treating the condition and that will exhibit an acceptable level of adverse events in a subpopulation.

In FIG. 1, the study data analysis system 102 is used by a clinical researcher 104. The clinical researcher 104 may, for example, use the study data analysis system 102 to enter, store, request, or access study data relating to a medical condition, treatment goal or prevention goal, such as, for example, the various examples provided herein. The clinical researcher 104 may generally represent, for example, a person involved in health care or the health care industry, including, for example, a pharmaceutical company researcher or clinician, a biotechnology company researcher or clinician, a doctor, or a medical researcher. The clinical researcher 104 also may represent someone who is involved in health care in the sense of developing, managing, or implementing the study data analysis system 102, e.g., a software developer with clinical knowledge (or access to clinical knowledge), a database manager, or an information technologies specialist. Even more generally, some or all of various functions or aspects described herein with respect to the clinical researcher 104 may be performed automatically, e.g., by an appropriately-designed and implemented computing device, or by software agents or other automated techniques.

Study data 106 is typically data relating to conditions of agent testing, agent dosing and administration schedule, delivery system, efficacy, mechanism(s) of action, adverse events, pharmacokinetics, pharmacodynamics, statistical parameters and outcomes, and/or other experimental condition or result. Study data 106 also may represent or include diagnostic testing, for example, to determine the safety and/or efficacy of a particular agent such as a medication, medical device or surgical treatment. Study data 106 may originate from, for example, an experiment and may be found in one or more different sources, including, for example, published journal articles, clinical trial reports, data reported on internet site(s), data submitted to the Food and Drug Administration or other regulatory agency, data included in pharmacogenomic database(s), data included in genetic database(s), or data found in other relevant database(s) that contain data relating to the conditions of use, effect, mechanism of action or other properties of an agent. Study data 106 may also originate from a mathematical and/or computer simulation(s) of one or more properties of an agent, for example, data from an in vitro/in vivo correlation analysis. Study data 106, for example, could result from pre-clinical testing or clinical testing, and may include data from in vitro testing, in situ testing, in vivo testing in animals or clinical testing in human subjects or patients. A formal clinical trial is one example of a study that results in study data 106.

Study data 106 may include raw data, for example, agent name, agent concentration, dosing, dosing frequency, agent concentration in the blood following administration at various times, minimum and maximum blood concentrations ($C_{min}$ and $C_{max}$, respectively), the times at which $C_{min}$ and $C_{max}$ occur ($T_{min}$ and $T_{max}$, respectively), measured effect of the agent(s) on blood protein, lipid or cell levels, and/or reported adverse events experienced by study participants.

Study data 106 may also include study participant information such as, for example, age, weight, gender, race, ethnicity, dietary factors, medical history, concomitant medications, and other demographic characteristics. Study data may also include molecular information about study participants such as, for example, genomic DNA sequence, cDNA sequence, single nucleotide polymorphisms (SNP's), haplotype profile, insertion and/or deletion (INDEL) profile, restriction fragment length polymorphism (RFLP) profile, chromatin state, nucleosome and/or histone/nucleoprotein composition, RNA sequence, micro RNA sequence, pyknon sequence and/or profile, RNA expression levels, protein sequence, protein expression levels, cytokine levels and/or activity, circulating hormone levels and/or activity, circulating carbohydrate levels, neurotransmitter levels, nitric oxide levels, liver enzyme expression and/or activity, gastrointestinal enzyme expression and/or activity, renal enzyme expression and/or activity, and/or other biochemical markers.

Study data 106 may include data points that are, for example, ordinals (e.g., $1^{st}$, $2^{nd}$, $3^{rd}$), nominals (e.g., nausea, congestive heart failure), binaries (e.g., alive/dead), genetic (e.g., AGCGGAATTCA), and/or continuous (e.g., 1-4, 5-10).

As a further example, the study data analysis system 102 can identify within study data 106 one or more subpopulation(s) having a defined efficacy level and a defined level of tolerance for one or more adverse events. Study data 106 may report efficacy levels and/or adverse event levels; such reported data may or may not precisely match actual efficacy levels and/or adverse event levels.

The study data analysis system 102 also can correlate subpopulation adverse event data with subpopulation identifier data to identify one or more clinically relevant patient populations. For example, an agent may be identified using the study data analysis system 102 that is effective and that exhibits tolerable adverse events in a subpopulation that is characterized by a particular molecular marker. The study data analysis system 102 may then be used to further search, for example, one or more population databases to find subpopulation identifier data 314 (FIG. 3) that correlate the molecular marker with one or more clinically relevant patient populations. Such population databases include, for example, those that contain molecular information about individuals or populations such as, for example, genomic DNA sequence, cDNA sequence, single nucleotide polymorphisms (SNP's), haplotype profile, insertion and/or deletion (INDEL) profile, restriction fragment length polymorphism (RFLP) profile, chromatin state, nucleosome and/or histone/nucleoprotein composition, RNA sequence, micro RNA sequence, pyknon sequence and/or profile, RNA expression levels, protein sequence, protein expression levels, cytokine levels and/or activity, circulating hormone levels and/or activity, circulating carbohydrate levels, neurotransmitter levels, nitric oxide levels, liver enzyme expression and/or activity, gastrointestinal enzyme expression and/or activity, renal enzyme expression and/or activity, and/or other biochemical markers.

Ongoing, prospective and completed clinical trials for various agents may be found at databases such as http://www.clinicaltrials.gov, which lists specific details for clinical trials, including primary and secondary outcomes, enrollment size, inclusion and exclusion criteria, and other parameters.

The study data analysis system 102 may apply appropriate statistical methods to study data 106, which may provide, for example, an average value(s) for a set of data, a confidence level(s) for a confidence interval(s), p-value(s), or other measures of statistical significance for multiple data points in one or more data sets, such as observed or simulated study data 106.

Accordingly, study data 106 relating to efficacy of an agent in terms of treating a medical condition often is associated with a statistical measure of significance in terms of, for example, a clinical endpoint of an experimental trial. For example, an agent administered to patients with a medical condition, according to a defined dosing schedule, may relieve one or more symptoms of the medical condition to an extent that is statistically significant when compared to the effect of a placebo.

Statistical analysis can be classified into two main groups: hypothesis testing and estimation. In hypothesis testing, a study typically compares the occurrence of one or more endpoints in two or more groups of participants. This often involves a comparison of the mean, proportion, or other data parameter of, for example, study efficacy data 306 (FIG. 3) in a test group to the same study efficacy data 306 (FIG. 3) in a control group. Study efficacy data, for example, may include measures such as the mean time to healing or pain relief, or the proportion of patients who showed a threshold degree of improvement at various times after administration of one or more agent(s).

In estimation, the goal is to determine the relative value of a characteristic of interest in a group under study. The estimated value is usually accompanied by a statement about its certainty, or confidence interval, which is expressed as a percentage. Estimation is important in hypothesis testing and in the analysis of safety variables. For example, in a study of a generic medication, where efficacy is equivalent to that of the reference medication, the FDA and the sponsor may be interested in estimating the proportion of patients that might experience a particular adverse event. To ensure that the estimate has a high probability of being accurate, the study data analysis system 102 would determine the confidence interval for it.

In the evaluation of study data, from whatever source, the character of the data is informative in terms of determining appropriate statistical measures to use to identify significant relationships and effects. The character of the data includes, for example, (1) the nature of the distribution of the primary, secondary, and influencing variables; (2) normal (Gaussian) or other well-known distributions; (3) if the data are not normally distributed, can they be changed by a function (e.g., a transformation) that preserves their order, but brings them into conformity with well-known assumptions about their distribution; (4) large enough sample size such that normality of the means can be assumed even if the data are not normally distributed; and/or (5) equality of variances of subgroups to be compared. These characteristics can be ascertained by applying common tests or by using basic data plots such as histograms or box plots. Knowing these characteristics of the data allows the study data analysis system 102 to validate the assumptions that underlie the data, and to select the most appropriate analytical method consistent with the data.

Study data 106 may, for example, contain two types of variables, quantitative and/or qualitative. Quantitative variables are numbers that can have, for example, a value within some acceptable range. For example, a person's blood pressure could be 120/80. Qualitative variables, however, typically lie within discrete classes, and are often characterized numerically by whole numbers. For instance, a patient who experiences nausea after agent administration could be characterized by a one, and a patient that does not could be classified as a zero.

The distribution of variables in a sample is important in determining what method of statistical analysis can be used. Normal, or Gaussian, distribution resembles the symmetrical bell-shaped curve by which most students are graded throughout their scholastic careers. It is typically characterized by two features: the mean, which is a measure of the location of the distribution, and the variance, which is a measure of the spread of the distribution. Many well-known statistical methods for analyzing means, such as the t-test or the paired t-test, rely on a normal distribution to ensure that the mean represents a measure of the center of the distribution.

Because statistical theory holds that the means of large samples are approximately normally distributed, an assumption of normality becomes less important as sample sizes increase. However, when sample sizes are small, it is important to determine whether the data to be analyzed are consistent with a normal distribution or with another well-characterized distribution.

Most common statistical tests of quantitative variables, including the t-tests and analysis of variance (ANOVA), are tests of the equality of the measures of location belonging to two or more subgroups that are assumed to have equal variance. A measure of location, such as a mean or median, is a single number that best describes the placement of the distribution (usually its center) on a number line. Because equal variance provides the basis of most tests that involve measures of location, in such cases an assumption of equal variance is more important than an assumption of normality, even when the tests do not rely on a specific distribution of the data (i.e., nonparametric tests). If the variances are not equal among the subgroups being compared, it is frequently possible to find a formula or function (e.g., a transformation) that preserves order and results in variables that do have equal variance.

When considering the distribution of data, it is also useful to look at a picture of them. The study data analysis system 102 can plot data to determine whether the distribution is shifted toward higher or lower values (skewed). The presence of one or more values that are much higher or lower than the main body of data indicates possible outliers. Data plots can also help to locate other data peculiarities. Common, statistically sound adjustment methods can be used to correct many types of data problems.

Once the character of the variables of interest has been established, the study data analysis system 102 can test for comparability between the treatment and control groups. Comparability is established by performing statistical tests to compare, for example, demographic factors, such as age at the time of the study, age at the time of disease onset, nationality, economic status, migration status, and/or gender; or prognostic factors measured at baseline, such as disease severity, concomitant medication, or prior therapies. Biased results can occur when the comparison groups show discrepancies or imbalances in variables that are known or suspected to affect primary or secondary outcome measures. For instance, when a group includes a large proportion of participants whose disease is less advanced than in those of a comparison group, the final statistical analysis will often show a more significant effect for the patients whose disease is less advanced, even though the effect may not be primarily caused by an administered agent.

For example, in a trial comparing the effectiveness of surgery and iodine-131 for treatment of hyperthyroidism, clinical researchers found that, surprisingly, patients who received the allegedly less-traumatic radiation therapy had a much higher frequency of illness and death than those who underwent surgery. Examination of the baseline characteristics of the two groups revealed that the patients selected for the surgery group were generally younger and in better health than those selected for the iodine treatment. The inclusion criteria for the surgery group were more stringent than those for the iodine group because the patients had to be able to survive the surgery.

It is desirable to perform comparability tests using as many demographic or prognostic variables simultaneously as the method of analysis will allow. The reason for using this approach is that the influence of a single, for example, demographic or prognostic characteristic on an outcome variable may be strongly amplified or diminished by the simultaneous consideration of a second characteristic. However, the size of many clinical trials is often insufficient to allow the simultaneous consideration of more than two variables. More commonly, the sample size of the study will allow consideration of only one variable at a time.

Imbalances detected in comparability testing do not necessarily invalidate study results. By tracking such differences, however, the study data analysis system 102 can account for their presence when comparing study data from treatment and control groups. Many statistical procedures can be used to adjust for imbalances either before or during an analysis, but such adjustments should be limited to cases where the extent of the difference is relatively small, as judged by a person of ordinary skill in the art.

Methods used for comprehensive analysis of study data vary according to the nature of the data, but also according to whether the analysis focuses on the effectiveness or the safety of the agent. Selection of an appropriate statistical method should also take into account the nature of the agent under study. For example, in vitro diagnostic studies may use statistical techniques that are somewhat specialized. Often the analysis is based on a specimen, such as a vial of blood, collected from a patient. The same specimen is typically analyzed by two or more laboratory methods to detect an analyte that is related to the presence of a condition or disease. Thus, each specimen results in a pair of measurements that are related to one another. The statistical treatment of such related (or correlated) data is very different from that of unrelated (or uncorrelated) data because both measurements are attempting to measure exactly the same thing in the same individual. Generally, if both laboratory measurements result in a quantitative variable, a first statistical analysis will attempt to measure the degree of relationship between the measurements. The usual practice is to perform a simple linear regression analysis that assumes that the pairs of values resulting from the laboratory tests are related in a linear way.

In linear regression analysis, a best-fit line through the data is found statistically, and the slope is tested to determine whether it is statistically different from zero. A finding that the slope differs from zero indicates that the two variables are related, in which case the correlation coefficient, a measure of the closeness of the points to the best-fit line, becomes important. A correlation coefficient with a high value, either positive or negative, indicates a strong linear relationship between the two variables being compared. However, this correlation is an imperfect measure of the degree of relationship between the two measurements. That is, although a good correlation with a coefficient near one may not indicate good agreement between the two measurements, a low correlation is almost surely indicative of poor agreement.

Although correlation can indicate whether there is a linear relationship between two study measurements, it does not provide good information concerning their degree of equivalence. Perfect equivalence would be shown if the correlation were very near one, the slope very near one, and the intercept very near zero. It is possible to have a very good relationship between the two measures, but still have a slope that is statistically very different from one and an intercept that is very different from zero. In such a situation, one of the two measurements may be biased relative to the other.

Another relevant analysis of study data is a relative risk assessment or a receiver operating characteristic (ROC) analysis. Software is available to perform either of these analyses. A relative risk assessment is a ratio of the risk of a condition among patients with a positive test value to the risk of the condition among patients with a negative test value. The relative risk analysis can be done by use of either a logistic regression or a Cox regression depending on whether the patients have constant or variable follow-up, respectively. ROC analysis provides a measure of the robustness of the cutoff value as a function of sensitivity and specificity.

Analysis of the effectiveness and/or safety of an agent typically involves hypothesis testing to determine whether the agent maintains or improves the health of patients in a safe way. In some cases, a particular agent may be compared to an agent of known function. In such cases, the result will be a test of the hypothesis that the unknown agent is better than or equal to the known agent. Selection of an appropriate statistical method for analysis of data from such studies depends on the answers to many questions, such as (1) is the primary variable quantitative or qualitative; (2) was the primary variable measured only once or on several occasions; (3) what other variables could affect the measurement under evaluation; and (4) are those other variables qualitative (ordered or not) or quantitative?

If the primary variable under evaluation is quantitative, selection of an appropriate method of analysis will depend on how many times that variable was measured and on the nature of any other variables that need to be considered. If there is only a single measurement for each variable, and there are no differences among the potential covariates belonging to the treated and control groups, the appropriate method of analysis may be a parametric or nonparametric ANOVA or t-test. For example, a study of a new cardiovascular agent that is expected to offer better protection against congestive heart failure ("CHF"), with all other things being equal, could compare six-month CHF rates of incidence by this method.

The choice of an appropriate analytical method changes if the covariates belonging to the two comparison groups differ and are measured qualitatively. Such cases may use a more complex analysis of variance or an analysis of covariance (ANCOVA). The ANCOVA method is particularly suited to analyzing variables that are measured before and after treatment, assuming that the two measurements are related in a linear or approximately linear manner. Using ANCOVA, the clinical researcher first adjusts the post-treatment measure for its relationship with the pre-treatment measure, and then performs an analysis of variance. Using the example of the cardiovascular agent, ANCOVA would be a suitable method of analysis if the amount of improvement in the six-month CHF rates of the patients treated by the agent depended, for example, on the patients' pre-treatment level of coronary artery blockage.

Outcome variables are often measured more than once for each study subject. When this is done, it should be done in a balanced way such that when a variable is measured it is measured for every patient. A balanced-repeated-measures ANOVA can be performed with or without covariates. With covariates, this method reveals the effect of each patient's covariate value on the outcome variable, the effect of time for each patient, and whether the effect of time for each patient is changed by different values of the covariate. Continuing with the CHF example, a repeated-measures ANOVA could be applied to evaluate measurements of coronary artery blockage before agent administration and at 3, 6, 9, and 12 months after initiation of dosing, and the number of coronary arteries that are at least 50% blocked. In this case, the primary outcome variable is the level of coronary artery blockage, and the covariate is the number of coronary arteries that are at least 50% blocked.

A repeated-measures ANOVA also can be used if a few patients missed a small number of measurements. However, in doing so the study data analysis system 102 may use other statistical algorithms known in the art in order to estimate the missing outcome measures.

Some studies result in a quantitative outcome variable and one or more quantitative covariates. In this situation, multiple regression methods are useful in evaluating outcome variables (called dependent variables), especially if the study involves several levels or doses of treatment as well as other factors (independent variables). Regression is a powerful analytical technique that enables the study data analysis system 102 to simultaneously assess the primary variables as well as any covariates.

The regression model is an equation in which the primary outcome variable is represented as a function of the covariates and other independent variables. The importance of each independent variable is assessed by determining whether its corresponding coefficient is significantly different from zero. If the coefficient is statistically greater than zero, then that independent variable is considered to have an effect on the dependent variable and is kept in the model; otherwise, it is discarded. The final model includes only those variables found to be statistically related to the dependent variable. The model enables the study data analysis system 102 to determine the strength of each independent variable relative to the others, as well as to the agent effect. In the CHF agent example, a multiple regression analysis would be appropriate for data where the level of coronary artery blockage was measured twice (e.g., at baseline and at 6 months), and the number of coronary arteries that are at least 50% blocked was measured as an independent variable.

For studies in which the outcome variable is qualitative, other types of analysis may be employed. Some of these resemble the methods used to analyze quantitative variables. For instance, log-linear modeling can be used to develop the same types of evaluations for a qualitative outcome variable as ANOVA and ANCOVA provide for quantitative measures.

Log-linear modeling techniques are equivalent to such commonly used Chi-square methods as the Cochran-Mantel-Haenzel method. They enable the study data analysis system 102 to compare the distribution of treatment and control patients within outcome classes; some techniques also make it possible to determine how consistent the influence of covariates is, and to adjust for that influence.

Because qualitative variables are represented by whole numbers, these methods may use special algorithms in order to estimate quantities of interest. Finding solutions for estimating those quantities can be accomplished readily with the aid of computer programs known in the art.

Logistic regression methods are the qualitative counterparts to the multiple regression techniques described for quantitative variables. While the two methods include models and interpretations that correspond closely, logistic regression computations are not as straightforward as those for multiple regression. Even so, they enable the study data analysis system 102 to determine relationships between the outcome variable and independent variables. Logistic regression allows the use of either quantitative or qualitative covariates, but it is preferred that study participants have a follow-up time that is essentially the same.

In logistic regression methods, a proportion is represented by a complex formula, a part of which is a multiple regression-like expression. By estimating the coefficients for the independent variables, including the agent administration, the study data analysis system 102 is able to determine whether a particular independent variable is statistically related to the dependent variable. The final model contains only these independent variables, the coefficients of which differ significantly from zero. Further, the logistic regression method estimates the odds ratio: a measure of the relative risk for each independent variable adjusted for the presence of the other variables. For example, if the agent were a special light designed to treat a fungus on the toenail, and if the logistic regression measured the rate of cure at 3 months after treatment, then an odds ratio of 7.9 for the treatment would imply that, adjusted for other variables in the final model, patients who had the treatment were 7.9 times more likely to experience a cure at 3 months than patients who did not have it.

The Cox regression method is another technique for analyzing qualitative outcome measures. This method can determine the effect of agents and other potential covariates even when the data do not have the same follow-up time. It yields a model and results that are analogous to those of the logistic regression method, but are not limited to patient survival outcomes. This method can be applied to, for example, an outcome that includes measurement of the time to a particular event, such as time to healing or cure. A powerful characteristic of the Cox regression method is that it keeps the study participant in the analysis until he or she drops out of the study. This can be an important factor in small studies, in which statistical power can be reduced when even a modest number of participants are unavailable for follow-up.

As in the case of effectiveness analyses, the selection of statistical methods appropriate for safety analyses depends on many factors. If the FDA and the clinical researcher have a great deal of knowledge about complications associated with a specific condition and its therapeutic agents, estimating the rate of complication with corresponding 95% confidence intervals may be appropriate. But if little is known about those complications, a more elaborate statistical treatment may be appropriate.

The most common method used to analyze complications is to compute freedom-from-complication rates by survival methods; one of the most commonly used analysis procedures for survival data is the Kaplan-Meier method. The popularity of this method is partly attributable to the fact that it measures the time to occurrence of a complication, and, like the Cox regression method, keeps participants in the life table until they drop out of a study. In addition, at the occurrence of each event, the Kaplan-Meier method provides an estimate of the event rate and its standard error, enabling the study data analysis system 102 to compute confidence intervals for each event.

A related method is the life table method, in which the study duration is divided into equal segments and the proportion of events and participant drop-outs is evaluated for each segment. For example, if the study had a one-year duration, the life table could be viewed as 12 one-month segments. Calculation of rates would depend on the number of participants that entered the study each month, the number of events that occurred in that month, the number of participants that dropped out of the study in that month, and the number of participants who went on to the next month. The event rate is calculated for each month rather than at the occurrence of each event, and the standard error is also determined, allowing for the computation of confidence intervals.

If it is necessary to test the hypothesis that two samples (such as a control and treated group) have the same complication experience for the study duration in the presence of covariates, this can be accomplished by comparing survival (freedom from complication) rates derived through use of the Cochran-Mantel-Haenzel method or an equivalent procedure. Cox regression provides a good method with which to determine the relative importance of covariates on a rate complication.

Such analytical methods are useful for comparing the rates at which a treated and control group encounter their first occurrence of a complication, but the occurrence of multiple complications or multiple occurrences of the same complication do not lend themselves readily to a single appropriate analytical technique. A combination of non-independent analyses is preferred to completely explain the effects of multiple events.

Numerical relationships detected as statistically significant by regression techniques are associations, not cause-and-effect relationships. To support the associative evidence provided by such analyses, the study data analysis system 102 may also make use of pre-clinical animal studies and other data that reinforce the determination of cause-and-effect, where available.

While it is generally desirable to prospectively design a study to provide statistically significant measures of efficacy and safety, retrospective analysis of study data 106 may provide adequate means for determining statistical relationships among the data. Alternatively, statistically significant measures of study data 106 may be unavailable in some cases. For example, an analysis of study data 106 may indicate an association between a small subset of patients enrolled in a clinical trial and a decreased incidence of an adverse event. Because of the small sample size of the subset of patients, the study data 106 may lack statistical power to indicate whether the association is statistically significant (e.g., the p-value may be >0.05). The association, however, may nevertheless be of interest by virtue of, for example, (1) magnitude of effect and/or (2) coincidence with a known mechanism of action of the agent. Therefore, the claimed subject matter should not be limited to study data analysis of, for example, a specific statistical level of significance. Many applications of the study data analysis system 102 exist, over and above the examples provided herein.

Study data 106 may include reported or calculated mean values of the parameters discussed above such as, for example, arithmetic, geometric and/or harmonic means. Study data may also include reported or calculated statistical measures such as student's t-test, p-value, chi square value(s), and/or confidence interval or level. Alternatively, the study data analysis system 102 may calculate an appropriate statistical measure using raw data.

In this regard, it should be understood that the herein claimed study data analysis system 102 can, for a given condition, (1) identify agents with a defined level of efficacy in the context of various reported or calculated statistical measures, (2) identify subpopulations that report or experience an adverse event at a defined level of tolerance, also in the context of various reported or calculated statistical measures (3) identify those subpopulations that also exhibit at least some level of efficacy in the context of various reported or calculated statistical measures, and (4) present the agent and/or subpopulation in response to the identification of the subpopulation.

For example, many databases may be searched singly or in combination to identify one or more agents that exhibit a desired level of effectiveness in treating a chosen condition. Similarly, many databases exist that may be searched singly or in combination to identify one or more subpopulations having a defined tolerance for at least one adverse event upon administration of the one or more agents. Similarly, many databases exist that may be searched singly or in combination to identify one or more subpopulations having a defined level of efficacy upon administration of the one or more agent.

Some conditions have a genetic component and are more likely to occur among people who trace their ancestry to a particular geographic area. People in an ethnic group often share certain versions of their genes, called alleles, which have been passed down from common ancestors. If one of these shared alleles contains a disease-causing mutation, a particular genetic disorder may be more frequently seen in that particular ethnic group than in others.

Examples of genetic conditions that are more common in particular ethnic groups are sickle cell anemia, which is more common in people of African, African-American, or Mediterranean heritage; and Tay-Sachs disease, which is more likely to occur among people of Ashkenazi (eastern and central European) Jewish or French Canadian ancestry.

Linkage disequilibrium (LD) is a term used in the field of population genetics for the non-random association of alleles at two or more genetic loci, not necessarily on the same chromosome. LD describes a situation in which some combinations of alleles or genetic markers occur more or less frequently in a population than would be expected from a random assortment of allelic sequences based on their frequencies. For example, in addition to having higher levels of genetic diversity, populations in Africa tend to have lower amounts of linkage disequilibrium than do populations outside Africa, partly because of the larger size of human populations in Africa over the course of human history and partly because the number of modern humans who left Africa to colonize the rest of the world appears to have been relatively low. In contrast, populations that have undergone dramatic size reductions or rapid expansions in the past and populations formed by the mixture of previously separate ancestral groups can have unusually high levels of linkage disequilibrium.

Linkage disequilibrium-based genome screening is a tool used to localize genes responsible for common diseases. This screening involves many more markers than traditional linkage studies and therefore presents the issue of defining an appropriate significance threshold that takes into account the consequent multiple comparisons. False Discovery Rate (FDR) has been used as a measure of global error in multiple tests for LD screening. Controlling FDR leads to an increased power to detect more than one locus, making this strategy particularly appealing for complex disease mapping. Such methods, including permutation-based evaluations of FDR within the sample of interest, for example, may be used to perform multivariate analyses among study data sets.

Databases that contain study data 106 relating to, for example, the genetic make-up of a population, agent efficacy, and/or agent adverse events include, for example, those found on the internet at the Entrez websites of the National Center for Biotechnology Information (NCBI). NCBI databases are internally cross-referenced and include, for example, medical literature databases such as PubMed and Online Mendelian Inheritance in Man; nucleotide databases such as GenBank; protein databases such as SwissProt; genome databases such as Refseq; and expression databases such as Gene Expression Omnibus (GEO). Also useful are publication databases such as Medline and Embase.

Other databases include, for example, IMS Health databases of prescribing information and patient reporting information such as that contained in the National Disease and Therapeutic Index (NDTI) database, which provides a large survey of detailed information about the patterns and treatment of disease from the viewpoint of office-based physicians in the continental U.S. Also of use is the U.S. Food and Drug Administration's (FDA's) Adverse Event Reporting System (AERS) database. This database contains adverse drug reaction reports from manufacturers as required by FDA regulation. In addition, health care professionals and consumers send reports voluntarily through the MedWatch program. These reports become part of a database. The structure of this database is in compliance with the international safety reporting guidance issued by the International Conference on Harmonization. The FDA codes all reported adverse events using a standardized international terminology called MedDRA (the Medical Dictionary for Regulatory Activities). Among AERS system features are the on-screen review of reports, searching tools, and various output reports. Another adverse drug events database is DIOGENES®, a database consisting of two sub-files: Adverse Drug Reactions (ADR) and Adverse Event Reporting System (AERS). ADR records contain data regarding a single patient's experience with a drug or combination of drugs as reported to the FDA. Since 1969, the FDA has legally-mandated adverse drug reaction reports from pharmaceutical manufacturers and maintained them in their ADR system. In November 1997, the ADR database was replaced by the AERS. Other adverse event reporting databases include, for example, the Vaccine Adverse Event Reporting System (VAERS) and the Manufacturer and User Facility Device Experience Database (MAUDE).

Figure 3:
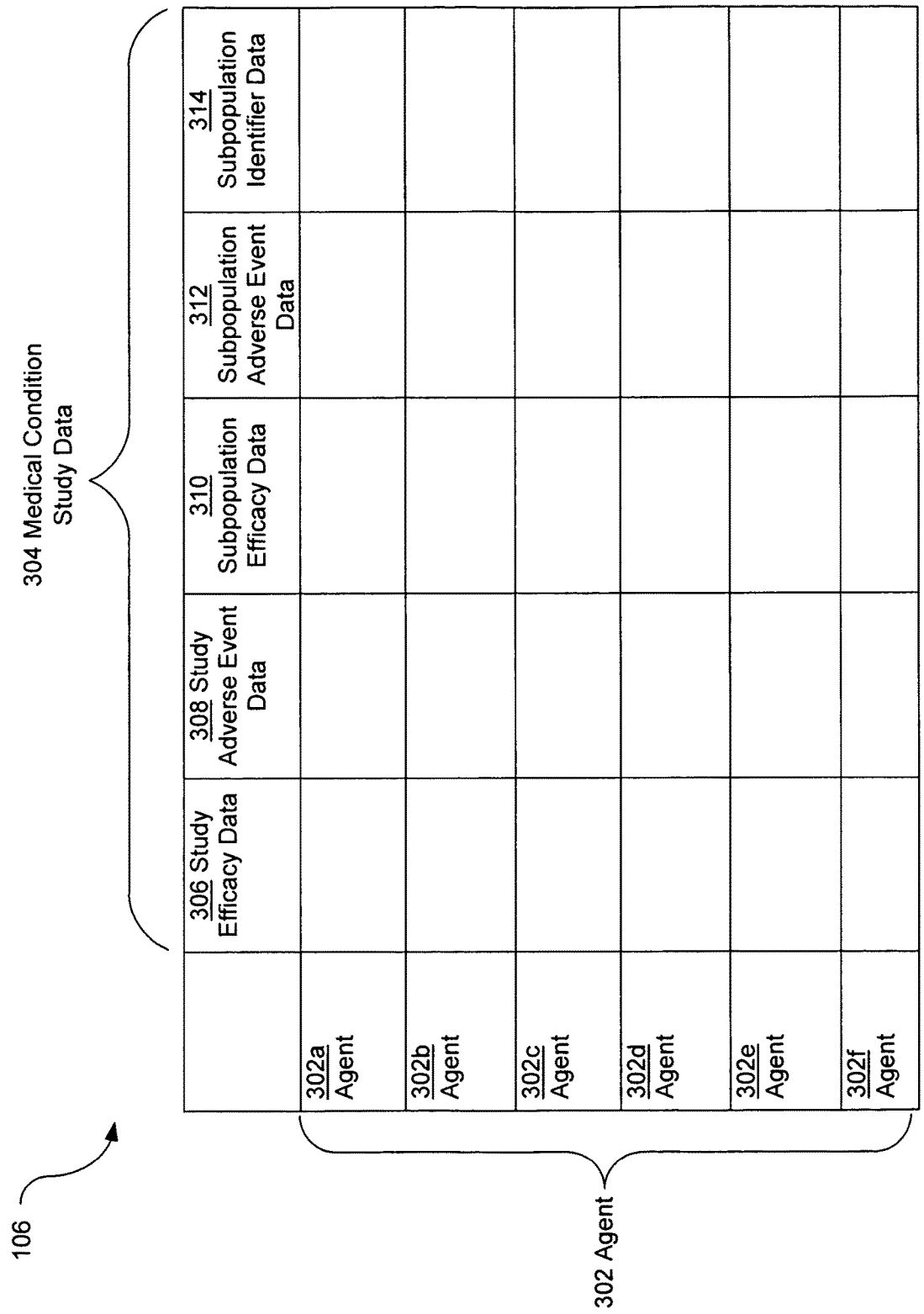
FIG. 3 illustrates an alternative embodiment of study data associated with the data analysis system of FIG. 1.

In one embodiment, the study data analysis system 102, having identified at least one agent 302 (FIG. 3) with defined efficacy in treating or preventing a condition, will then proceed to identify one or more subpopulations with a defined tolerance for at least one adverse event associated with administration of the at least one agent 302 (FIG. 3). In doing so, the study data analysis system 102 may identify a subpopulation characterized by, for example, one or more molecular parameters such as DNA sequence, protein sequence, or protein expression level. The study data analysis system 102 may then confirm that the subpopulation exhibits at least some defined level of efficacy upon administration of the at least one agent 302 (FIG. 3) to the subpopulation.

Data or parameters characterizing a population or subpopulation, as described and claimed herein, refers generally to data regarding a population or subpopulation. For example, data characterizing a population or subpopulation may be, for example, reported in the scientific literature, self-reported, measured, reported in survey results, present in archival documentation and/or anecdotal.

A subpopulation characterized by, for example, one or more molecular profiles may not, at first glance, correspond to a known, clinically-defined segment of the global or a national population. The study data analysis system 102 may therefore perform the additional step of correlating the subpopulation molecular profile with molecular profiles of known ethnic, gender, age or other demographic feature. For example, a subpopulation characterized by a specific DNA sequence may be screened against an ethnic genomic DNA database(s) to identify an ethnic group in which the specific DNA sequence is more common than in the general population. Such an ethnic population may accordingly be identified as of increased interest for further study as possible beneficiaries of treatment with the agent in question.

Additionally, the claimed subject matter may be used with a medical device(s) as the agent 302 (FIG. 3). For example, MAUDE, mentioned above, may be searched to identify a subpopulation(s) in which an agent 302 (FIG. 3), in this case a medical device, is both effective in treating a condition and safe with respect to a defined level of tolerance in the context of one or more specific adverse events. MAUDE data represents reports of adverse events involving medical devices. The data consists of voluntary reports since June 1993, user facility reports since 1991, distributor reports since 1993, and manufacturer reports since August 1996.

Surgical intervention may also be a claimed agent 302 (FIG. 3). For example, surgical ovarian ablation, in which the ovaries are removed to reduce the risk of breast cancer in pre-disposed populations, is associated with important adverse events such as hot flashes, impaired sleep habits, vaginal dryness, dyspareunia, and increased risk of osteoporosis and heart disease. Through use of the systems claimed herein, subpopulations may be identified for which the incidence of such adverse events is lower. For example, subpopulations of women taking hormone replacement therapy (HRT) may be better candidates for ovarian ablation due to the effects of HRT such as, for example, decreased risk of osteoporosis and heart disease. Thus, ovarian ablation may be identified and presented as an agent that is effective and associated with a decreased incidence of certain adverse events in certain subpopulations of women.

Although many other examples are provided herein and with reference to the various figures, it should be understood that many types and instances of study data 106 may play a role in the use and application of the various concepts referenced above and described in more detail herein. The study data analysis system 102 may store such study data 106 in a database 136 or other memory, for easy, convenient, and effective access by the clinical researcher 104.

The study data 106 may include, for example, not only the clinical study data and/or the corresponding efficacy and adverse event data, but also various other parameters and/or characteristics related to subjects or patients to whom an agent 302 (FIG. 3) has been administered, examples of which are provided herein. Through detailed storage, organization, and use of the study data 106, the clinical researcher 104 may be assisted in identifying optimal subpopulations and agents, in order, for example, to find a new target population for an otherwise under-utilized agent 302 (FIG. 3). Ordered assignment and/or storage of information within the study data 106, as described herein, facilitates and/or enables such recall, access, and/or use of the study data 106 by the clinical researcher 104 in identifying the subpopulation, agent, and/or subpopulation identifier data.

In the study data analysis system 102, agent identification logic 126 and/or subpopulation identification logic 128 may be used to store, organize, access, recall, or otherwise use the information stored in the study data 106. For example, the agent identification logic 126 may access a database management system (DBMS) engine 130, which may be operable to perform computing operations to insert or modify new data into/within the study data 106, perhaps in response to new research or findings, or in response to a preference of the clinical researcher 104. For example, if a new agent is discovered to be effective in a certain condition, the clinical researcher 104 may access the study data analysis system 102 and/or agent identification logic 126 and/or subpopulation identification logic 128 through a user interface 132, in order to use the DBMS engine 130 to associate the new agent with one or more subpopulations for which the incidence of a specific adverse event is acceptable, i.e., effective at a defined tolerance level. As another example, if data from a new study, e.g., a clinical trial report, indicate that an agent 302 (FIG. 3) is effective and safe in a subpopulation that was not specifically identified in the clinical trial report by the trial sponsors, the study data analysis system 102 and/or supbpopulation identification logic may identify that subpopulation and present the agent 302 (FIG. 3) to a user interface 132 in response to a query from a clinical researcher 104.

Similarly, in a case where a clinical researcher 104 seeks, for example, to identify an agent(s) 302 (FIG. 3) that is safe and effective for administration to patients according to a specific profile, the clinical researcher 104 may access the user interface 132 to use the agent identification logic 126, subpopulation identification logic 128 and/or DBMS Engine 130 to find an agent(s) 302 that fits the profile and/or to find an agent(s) 302 (FIG. 3) that may be promising for further study. For example, if a specific treatment for a medical condition is typically associated with an unacceptable level of a specific adverse event, then the clinical researcher 104 may input this information via the user interface 132 in order to obtain one or more options for treating or preventing the condition in one or more subpopulations that exhibit acceptable levels of the specific adverse event.

As another example, if a clinical researcher 104 is interested in medical condition X, then the clinical researcher 104 may search for agents 302 (FIG. 3) that are effective in treating medical condition X, and subpopulations in which administration of the agents 302 (FIG. 3) does not result in unacceptable levels of a specific adverse event. The agent identification logic 126 and/or subpopulation identification logic 128 may then interface with the DBMS engine 130 to obtain, from the study data 106, one or more subpopulations that exhibit an adverse event profile at a specified tolerance level and an efficacy profile at some defined level. In this case, once the subpopulation is identified, the study data analysis system 102 and/or agent identification logic 126 and/or subpopulation identification logic 128 would present the agent(s) 302 (FIG. 3) to the user interface 132 and the clinical researcher 104 as one(s) that meets the input criteria.

It should be understood that adverse event data may represent effects of an agent 302 (FIG. 3) itself and/or effects of a delivery system associated with an agent 302 (FIG. 3). For example, in the case of an agent 302 (FIG. 3) administered via liposomal delivery, the liposomes themselves may give rise to adverse events such as accumulation in the liver and spleen, and extravasation into non-target tissues. The present systems may be used to identify subpopulations and agents for which such delivery system adverse events are tolerable.

As a general matter, a clinical researcher 104, e.g., a pharmaceutical scientist or a biomedical researcher, may not be aware of all currently available content of the study data 106. Thus, the study data analysis system 102 and/or agent identification logic 126 and/or subpopulation identification logic 128 provides the clinical researcher 104 with fast, accurate, current, and/or comprehensive efficacy and adverse event information, and also provides techniques to ensure that the information remains accurate, current, and/or comprehensive, by allowing the addition and/or modification of the existing study data 106, as new study information becomes available.

In FIG. 1, the study data analysis system 102 is illustrated as possibly being included within a clinical research device 134. The clinical research device 134 may include, for example, a mobile computing device, such as a personal digital assistant (PDA), or a laptop computer. Of course, virtually any other computing device may be used to implement the study data analysis system 102, such as, for example, a workstation, a desktop computer, or a tablet PC.

Additionally, not all of the study data analysis system 102 need be implemented on a single computing device. For example, the study data 106 may be stored on a remote computer, while the user interface 132 and/or agent identification logic 126 and/or subpopulation identification logic 128 are implemented on a local computer. Further, aspects of the study data analysis system 102 may be implemented in different combinations and implementations than that shown in FIG. 1. For example, functionality of the DBMS engine 130 may be incorporated into the agent identification logic 126 and/or the subpopulation identification logic 128 and/or the study data 106. Agent identification logic 126 and/or the subpopulation identification logic 128 may include, for example, fuzzy logic and/or traditional logic steps. Further, many methods of searching databases may be used, including, for example, unsupervised pattern discovery methods, coincidence detection methods, and/or entity relationship modeling.

The study data 106 may be stored in virtually any type of memory that is able to store and/or provide access to information in, for example, a one-to-many, many-to-one, and/or many-to-many relationship. Such a memory may include, for example, a relational database and/or an object-oriented database, examples of which are provided in more detail herein.

Figure 2:
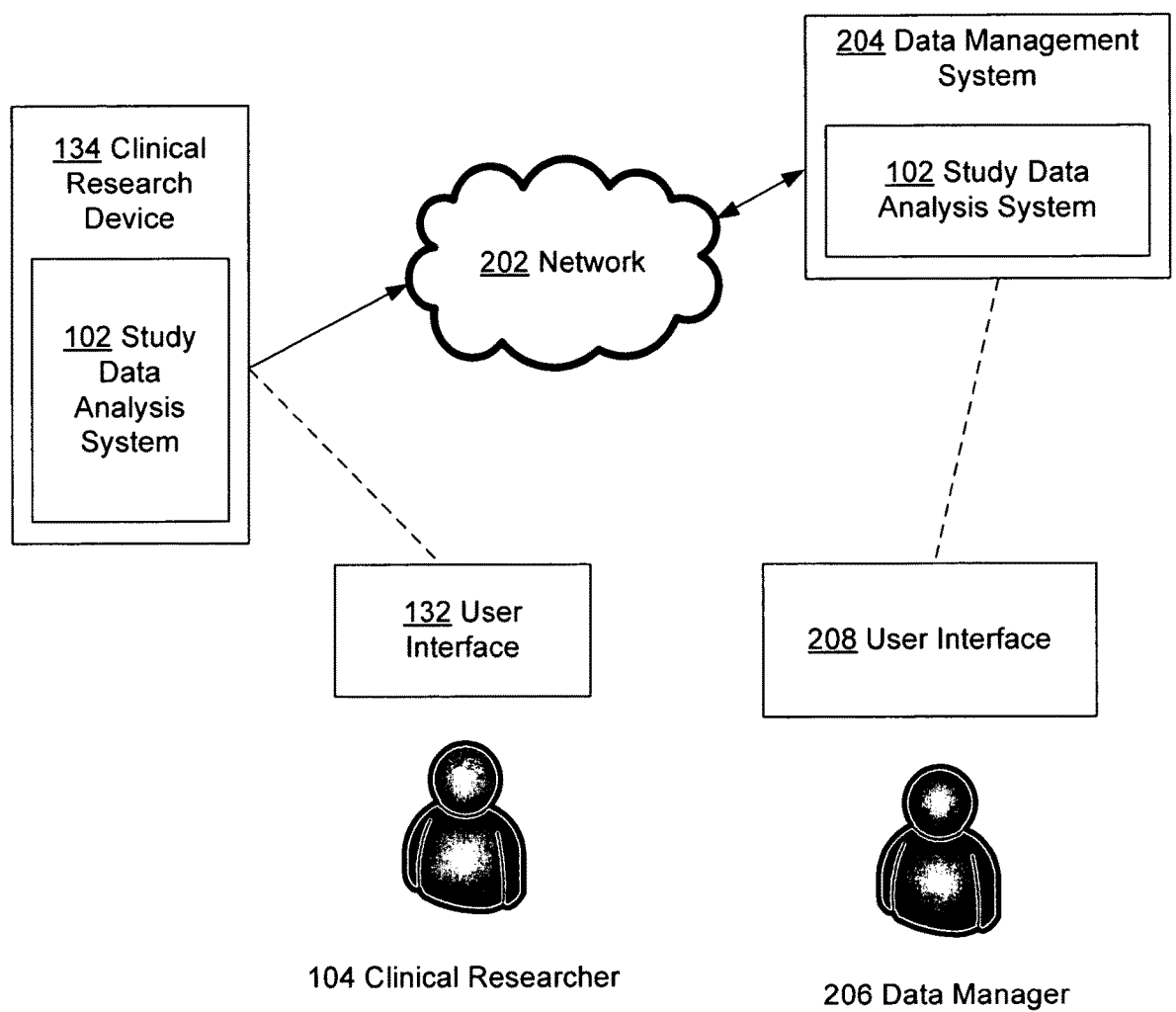
FIG. 2 illustrates certain alternative embodiments of the data analysis system of FIG. 1.

FIG. 2 illustrates certain alternative embodiments of the research system 100 of FIG. 1. In FIG. 2, the clinical researcher 104 uses the user interface 132 to interact with the study data analysis system 102 deployed on the clinical research device 134. The clinical research device 134 may be in communication over a network 202 with a data management system 204, which may be also running the study data analysis system 102; the data management system 204 may be interacted with by a data manager 206 through a user interface 208. Of course, it should be understood that there may be many clinical researchers other than the specifically-illustrated clinical researcher 104, each with access to an individual implementation of the study data analysis system 102. Similarly, multiple data management systems 204 may be implemented.

In this way, the clinical researcher 104, who may be operating in the field, e.g., in an office, laboratory and/or hospital environment, may be relieved of a responsibility to update or manage contents in the study data 106, or other aspects of the study data analysis system 102. For example, the data management system 204 may be a centralized system that manages a central database of the study data 106, and/or that deploys or supplies updated information from such a central database to the clinical research device 134.

FIG. 3 illustrates an alternative embodiment of the study data 106 associated with the research system 100 of FIG. 1. In FIG. 3, and in the various examples herein, a particular nomenclature is used for the terms described above and related terms, in order to provide consistency and clarity of description. However, it should be understood that other terminology may be used to refer to the same or similar concepts.

In FIG. 3, agents 302 are stored and organized with respect to a plurality of medical condition study data 304. The medical condition study data 304 include many of the terms and concepts just described, as well as additional, but not exhaustive, terms and concepts that may be relevant to a use and operation of the study data analysis system 102.

For example, the medical condition study data 304 include study efficacy data 306. Study efficacy data 306 may refer, for example, to data resulting from administration or testing of an agent(s) 302 that relates to an intended effect. Study adverse event data 308 may refer, for example, to data resulting from administration or testing of an agent(s) 302 that relates to an unintended effect. For example, study efficacy data 306 may include remission rates following administration of an anti-cancer agent. Study adverse event data 308 may include, for example, incidence of nausea or bone pain following administration of an anti-cancer agent.

Somewhat analogously, subpopulation efficacy data 310 refers to, for example, data resulting from administration or testing of an agent(s) 302 that relates to an intended effect of the agent(s) in a subpopulation. A subpopulation may include one or more individuals or one or more groups of individuals. Subpopulation efficacy data 310, for example, includes remission rates for females only following administration of an anti-cancer agent. In this example, females are the subpopulation.

Similarly, subpopulation adverse event data 312 refers to, for example, data resulting from administration or testing of an agent(s) 302 that relates to an unintended effect of the agent(s) in a subpopulation. Subpopulation adverse event data 312 may include, for example, elevated blood pressure or decreased interleukin-12 expression following administration of an anti-cancer agent. Subpopulation adverse event data 312, for example, may include incidence of nausea or bone pain for females only following administration of an anti-cancer agent. Accordingly, subpopulation adverse event data may be data characterizing the adverse event itself and/or data characterizing the subpopulation experiencing the adverse event.

Medical condition study data 304 may also include subpopulation identifier data 314. Subpopulation identifier data 314 may refer, for example, to data that tends to distinguish the subpopulation from other subpopulations or a general population, other than subpopulation adverse event data 312. Subpopulation identifier data 314, for example, may include a genomic DNA sequence that is specific to a subpopulation and which tends to distinguish that subpopulation from other subpopulations or a general population. Subpopulation identifier data 314 may correlate with subpopulation adverse event data 312 and/or further characterize the subpopulation.

Accordingly, the study data analysis system 102 may be used to identify one or more agents exhibiting (1) study efficacy data 306 in the context of administration or testing of one or more medical conditions, at a level defined by a clinical researcher 104; and (2) subpopulation adverse event data 312 at a level defined by a clinical researcher 104. As discussed above, identification of such an agent involves the identification of a subpopulation that may be characterized by subpopulation identifier data 314.

In an alternative embodiment, subpopulation identifier data 314 may be used as a parameter for use in searching one or more biomedical databases to identify clinically relevant population(s) that correlate with the subpopulation identifier data 314. For example, using the study data analysis system 102 and/or agent identifier logic 126 and/or subpopulation identifier logic 128, an agent may be identified that is acceptably effective and safe in a subpopulation characterized by, for example, a specific haplotype profile. That specific haplotype profile may then be used as a search parameter to screen biomedical databases for prospective patient populations that display the specific haplotype profile, e.g., individuals with primarily Mediterranean ancestry. The study data analysis system 102 and/or agent identifier logic 126 and/or subpopulation identifier logic 128 may perform this analysis. The subsequently-identified prospective patient population (individuals with primarily Mediterranean ancestry) is thus a candidate for further testing as a potentially viable population that could benefit from the identified agent 302 with an acceptable incidence of adverse events.

Many other examples of relationships and associations between the various medical condition study data 304 and/or the agent(s) 302 may be defined or determined and stored in the study data 106 according to the agent identification logic 126 and the subpopulation identification logic 128. Certain of these examples are provided herein.

Additionally, although the study data 106 is illustrated conceptually in FIG. 3 as a flat table in which one or more of the selected agents 302 are associated with one or more of the medical condition study data 304, it should be understood that this illustration is for explanation and example only, and is not intended to be limiting in any way with respect to the various ways in which the study data 106 may be stored, organized, accessed, recalled, or otherwise used.

For example, the study data 106 may be organized into one or more relational databases. In this case, for example, the study data 106 may be stored in one or more tables, and the tables may be joined and/or cross-referenced in order to allow efficient access to the information contained therein. Thus, the agent(s) 302 may define a record of the database(s) that are associated with various ones of the medical condition study data 304.

In such cases, the various tables may be normalized so as, for example, to reduce or eliminate data anomalies. For example, the tables may be normalized to avoid update anomalies (in which the same information would need to be changed in multiple records, and which may be particularly problematic when database 136 is large), deletion anomalies (in which deletion of a desired field or datum necessarily but undesirably results in deletion of a related datum), and/or insertion anomalies (in which insertion of a row in a table creates an inconsistency with another row(s)). During normalization, an overall schema of the database 136 may be analyzed to determine issues such as, for example, the various anomalies just referenced, and then the schema is decomposed into smaller, related schemas that do not have such anomalies or other faults. Such normalization processes may be dependent on, for example, desired schema(s) or relations between the agent(s) 302 and/or medical condition study data 304, and/or on desired uses of the study data 106.

Uniqueness of any one record in a relational database holding the study data 106 may be ensured by providing or selecting a column of each table that has a unique value within the relational database as a whole. Such unique values may be known as primary keys. These primary keys serve not only as the basis for ensuring uniqueness of each row (e.g., agent) in the database, but also as the basis for relating or associating the various tables within one another. In the latter regard, when a field in one of the relational tables matches a primary key in another relational table, then the field may be referred to a foreign key, and such a foreign key may be used to match, join, or otherwise associate (aspects of) the two or more related tables.

FIG. 3 and associated potential relational databases represent only one example of how the study data may be stored, organized, accessed, recalled, or otherwise used.

Figure 4:
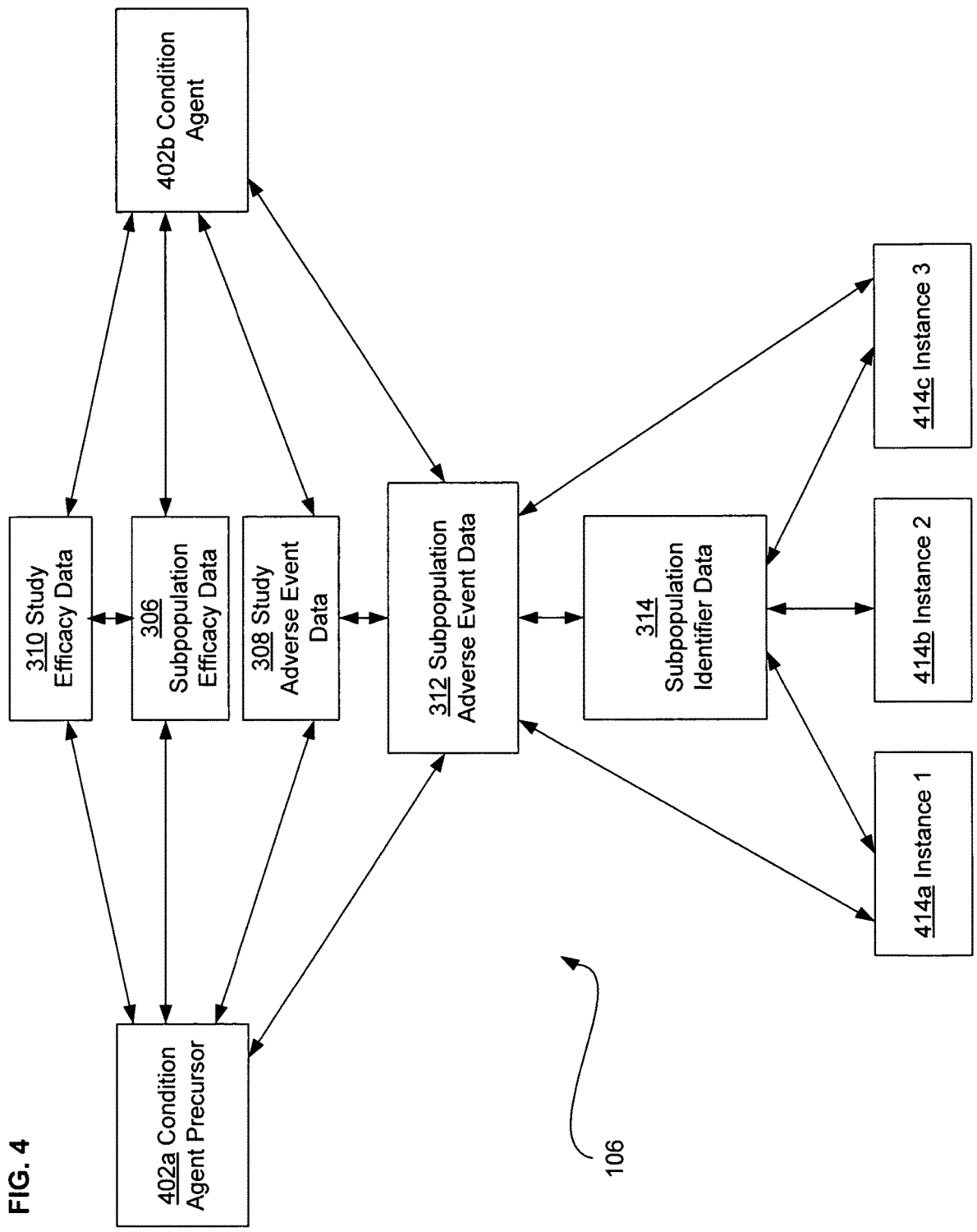
FIG. 4 illustrates another alternative embodiment of study data associated with the data analysis system of FIG. 1.

FIG. 4 illustrates another alternative embodiment of study data 106 associated with the research system 100 of FIG. 1, in which the study data 106 is conceptually illustrated as being stored in an object-oriented database.

In such an object-oriented database, the various agent(s) 302 and/or medical condition study data 304 may be related to one another using, for example, links or pointers to one another. FIG. 4 illustrates a conceptualization of such a database structure in which the various types of study data are interconnected, and is not necessarily intended to represent an actual implementation of an organization of the study data 106.

The concepts described above may be implemented in the context of the object-oriented database of FIG. 4. For example, two instances 302*a* and 302*b* of the agent 302 may be associated with study efficacy data 306 and study adverse event data 308. An agent(s) 302 or instance of one or more agent(s) that exhibits a desired level of efficacy and a defined level of tolerance for one or more adverse events may be associated with one or more subpopulations characterized by subpopulation adverse event data 312. For example, condition agent 302*b* may be associated with subpopulation adverse event data 312 indicating an acceptable adverse event profile.

Similarly, subpopulation adverse event data 312 may be associated with subpopulation identifier data 314. For example, subpopulation adverse event data 312 associated with condition agent 302*b* may be associated with subpopulation identifier data 314. Further, three instances of subpopulation identifier data, for example instance 1 (414*a*), instance 2 (414*b*), and instance 3 (414*c*), may be associated with the subpopulation identifier data 314 and/or the subpopulation adverse event data 312.

Also, other data may be included in the study data 106. For example, in FIG. 4, a condition agent precursor 402*a* is shown that refers generally to an agent used to facilitate application of the agent 302, e.g., a substance that when metabolized becomes condition agent 302, such as with prodrugs.

Many other examples of databases and database structures also may be used. Other such examples include hierarchical models (in which data is organized in a tree and/or parent-child node structure), network models (based on set theory, and in which multi-parent structures per child node are supported), or object/relational models (combining the relational model with the object-oriented model).

Still other examples include various types of eXtensible Mark-up Language (XML) databases. For example, a database may be included that holds data in some format other than XML, but that is associated with an XML interface for accessing the database using XML. As another example, a database may store XML data directly. Additionally, or alternatively, virtually any semi-structured database may be used, so that context may be provided to/associated with stored data elements (either encoded with the data elements, or encoded externally to the data elements), so that data storage and/or access may be facilitated.

Such databases, and/or other memory storage techniques, may be written and/or implemented using various programming or coding languages. For example, object-oriented database management systems may be written in programming languages such as, for example, C++ or Java. Relational and/or object/relational models may make use of database languages, such as, for example, the structured query language (SQL), which may be used, for example, for interactive queries for information and/or for gathering and/or compiling data from the relational database(s).

As referenced herein, the study data analysis system 102 and/or agent identification logic 126 and/or subpopulation identification logic 128 may be used to perform various data querying and/or recall techniques with respect to the study data 106, in order to facilitate discovery of a suitable agent 302. For example, where the study data is organized, keyed to, and/or otherwise accessible using one or more of the agents 302 and/or medical condition study data 304, various Boolean, statistical, and/or semi-boolean searching techniques may be performed.

For example, SQL or SQL-like operations over one or more of the agents 302/medical condition study data 304 may be performed, or Boolean operations using the agents 302/medical condition study data 304 may be performed. For example, weighted Boolean operations may be performed in which different weights or priorities are assigned to one or more of the agents 302/medical condition study data 304, perhaps relative to one another. For example, a number-weighted, exclusive-OR operation may be performed to request specific weightings of desired (or undesired) study data to be included (excluded).

The clinical researcher 104 may wish to determine examples of one or more agents 302 that are associated with examples of study adverse event data 308 that belong to a particular class, for example, neurological, gastrointestinal, and/or cardiovascular adverse events. For example, the clinical researcher 104 may want to identify agents 302 that may be effective in relieving arthritis pain, but for which cardiovascular adverse events are unacceptable. Having identified a set of agents meeting these criteria, the clinical researcher 104 could then use the study data analysis system 102 to query the subpopulation adverse event data 312 to identify subpopulations exhibiting acceptable levels of cardiovascular adverse events. In other examples, the clinician may be willing to tolerate lower levels of efficacy with the intention that more and/or different subpopulations may be identified for which an agent exhibits acceptable cardiovascular adverse events.

As another example, the clinical researcher 104 may start with a preferred subpopulation, characterized by either subpopulation identifier data 314 or subpopulation adverse event data 312, and proceed to identify agents that are effective and safe for that subpopulation.

The clinical researcher 104 may specify such factors using, for example, the user interface 132. For example, the clinical researcher 104 may be able to designate one or more of the agents 302/medical condition study data 304, and assign a weight or importance thereto, using, for example, a provided ranking system. In this regard, and as referenced herein, it should be understood that the clinical researcher 104 may wish to deliver a particular instance of an agent 302, e.g., a particular chemotherapeutic to be delivered to a tumor. However, such an otherwise effective agent, if applied by conventional techniques, may present an unacceptable level of nausea and/or pain following administration. Moreover, the clinical researcher 104 may not be aware of a subpopulation of prospective patients that may tolerate the agent better than previously-examined population(s). However, the clinical researcher 104 may query the study data analysis system 102 based on the desired agent 302, and may thereby discover one or more subpopulations in which the agent may be applied without unacceptable adverse events. The clinical researcher 104 may further query the study data analysis system 102 based on the subpopulation adverse event data 312 to elicit subpopulation identifier data 314 that describe one or more clinically relevant prospective patient subpopulations.

Similarly, data analysis techniques (e.g., data searching) may be performed using the study data 106, perhaps over a large number of databases. For example, the clinical researcher 104 may input some medical condition of interest for which the incidence of specific adverse events under the existing standard of care is high and/or unacceptable. Then, the clinician should receive a listing of agents that are ranked according to some criteria. For example, the clinical researcher 104 may receive a listing of instances of agents 302, ordered by efficacy, incidence of a particular adverse event in a tested general population, and incidence of a particular adverse event in a tested subpopulation. In this way, for example, if a set of agents 302 is effective according to the criteria of the clinical researcher 104, then the clinical researcher 104 may select an agent 302 according to acceptable incidence of adverse event(s), even if some relative sacrifice of efficacy is associated with such a selection.

By way of further example, other parameters/characteristics may be factored in. For example, elimination pathways may be tracked, databased, and/or weighted for use in the study data 106 and/or the study data analysis system 102. For example, if a particular agent 302 is easily eliminated by the liver, then, in a case where a subpopulation is identified that is characterized by compromised liver function, such an agent may be selected by the clinical researcher 104, even if an otherwise more effective agent 302 is known. Algorithms implementing such query/recall/access/searching techniques may thus use Boolean or other techniques to output, for example, a thresholded, rank-ordered list. The agent identification logic 126 and/or subpopulation identification logic 128 may then assign a key or other identifier to such a list(s), for easier use thereof the next time a like query is performed.

Design and testing of querying techniques in particular implementations of the study data analysis system 102 may involve, for example, entry of candidate agents 302/medical condition study data 304 (or instances thereof) into a database(s), along with associated test results and/or affinity metrics that may be used to determine/weight targets or sets of targets. Then, an identifier may be generated that is unique to the target(s) set(s).

FIG. 5 illustrates another alternative embodiment of study data associated with the research system 100 of FIG. 1, with specific examples of study data. In particular, FIG. 5 provides or refers to example results from a related technical paper, which is specifically referenced below.

For example, the first and second rows of the table of FIG. 5 (i.e., rows 502 and 504, respectively) refer to examples that may be found in Niyikiza et al., "Homocysteine and Methylmalonic Acid: Markers to Predict and Avoid Toxicity from Pemetrexed Therapy," Mol. Canc. Ther., vol. 1, pp. 545-552 (May 2002), which is hereby incorporated by reference in its entirety, and which may be referred to herein as the Niyikiza reference.

In the Niyikiza reference, data are reported for various treatment populations, characterized by a number of measured clinical parameters, which provide a basis for correlating an adverse event frequency or odds ratio with a predictive factor for severe toxicity in a patient population, for a specific agent in the treatment of specific medical conditions.

The Niyikiza reference, for example, reports data showing that the toxicity of the agent pemetrexed, a multi-targeted antifolate treatment for various cancers, correlates with high levels of homocysteine and methylmalonic acid, which are indicative of deficient levels of folic acid and vitamin B12. Inside a cell, pemetrexed is rapidly metabolized into active polyglutamate forms that are potent inhibitors of several tetrahydrofolate cofactor-requiring enzymes critical to the synthesis of purines and thymidine. Functionally, pemetrexed acts as a prodrug for its intracellular polyglutamate forms.

Rows 502 and 504 represent fields of data reported for pemetrexed (trade name "Alimta"). The Niyikiza reference examined data from studies of pemetrexed administration to 246 patients treated between 1995 and 1999. Multivariate stepwise regression methods were used to identify markers predictive of severe toxicity. An odds ratio approach was used to correlate a potential predictive marker with a risk of developing severe toxicity. As shown in rows 502 and 504, an odds ratio of 1 correlates with study adverse event data 308 from the overall study population. The Niyikiza reference reports subpopulation adverse event data 312 that, for a subpopulation in which methylmalonic acid levels are less than 119.0 nmol/l, the odds ratio of developing severe toxicity is 0.3. Similarly, a subpopulation with total homocysteine levels of less than 7.5 μmol/l had an odds ratio of developing severe toxicity of 0.7. This subpopulation adverse event data 312 was further correlated with subpopulation identifier data 314 indicating that patients supplemented with folic acid and vitamin B12 would likely exhibit the desired subpopulation adverse event data 312. The Niyikiza reference also reports subpopulation efficacy data 310 that members of the identified subpopulation had maintained or improved efficacy following administration of pemetrexed.

FIG. 6 illustrates another alternative embodiment of study data associated with the research system 100 of FIG. 1, with specific examples of study data. In particular, FIG. 6 provides or refers to example results from a related technical paper, which is specifically referenced below.

For example, the first through third rows of the table of FIG. 6 (i.e., rows 602, 604, and 606, respectively) refer to examples that may be found in Vogelzang et al., "Phase III Study of Pemetrexed in Combination With Cisplatin Versus Cisplatin Alone in Patients With Malignant Pleural Mesothelioma," J. Clin. Oncol., vol. 21:14, pp. 2636-44 (Jul. 15, 2003), which is hereby incorporated by reference in its entirety, and which may be referred to herein as the Vogelzang reference.

In the Vogelzang reference, data are reported for various treatment populations which provide a basis for correlating an agent with a predictive factor for severe toxicity in a patient population. The Vogelzang reference, for example, reports data showing that a subpopulation supplemented with folic acid and vitamin B12 experiences less toxicity following administration of pemetrexed, based on the hypothesis developed in the Niyikiza reference that the agent may have particularly detrimental effects in patients with high levels of homocysteine and methylmalonic acid, which are indicative of deficient levels of folic acid and/or vitamin B12.

Rows 602, 604 and 606 contain study data from the Vogelzang reference, showing study data from a phase III clinical trial comparing efficacy and adverse events following administration of pemetrexed plus cisplatin for malignant pleural mesothelioma versus administration of cisplatin alone. Study efficacy data 306 from the intent to treat group showed a significant benefit in efficacy with the combination therapy. Subpopulation efficacy data 310 from the group that was fully supplemented with folic acid and vitamin B12 showed a significant benefit in efficacy with the combination therapy, similar to that of study efficacy data 306.

Subpopulation adverse event data 312 from the Vogelzang reference for three different parameters are also shown in rows 602, 604 and 606, respectively. The subpopulation adverse event data 312 in row 602 is a reported 23.2% grade ¾ neutropenia for the group that was given full supplementation with folic acid and vitamin B12. This is down from 41.4% grade ¾ neutropenia in the group that was partially or never supplemented with folic acid and vitamin B12.

The subpopulation adverse event data 312 in row 604 is a reported 11.9% nausea for the group that was given full and partial supplementation with folic acid and vitamin B12. This is down from 31.3% nausea in the group that was never supplemented with folic acid and vitamin B12.

The subpopulation adverse event data 312 in row 606 is a reported 10.3% vomiting for the group that was given full and partial supplementation with folic acid and vitamin B12. This is down from 31.3% vomiting in the group that was never supplemented with folic acid and vitamin B12.

Thus, many parameters may be screened as subpopulation adverse event data 312 for a given agent. Moreover, the Vogelzang reference also describes the three subpopulations identified by subpopulation adverse event data 312 in terms of populations that are supplemented with folic acid and vitamin B12 (i.e., subpopulation identifier data 314 in rows 602, 604 and 606).

FIG. 7 illustrates hypothetical alternative embodiments of study data associated with the research system 100 of FIG. 1, with specific examples of study data. In particular, FIG. 7 provides or refers to an example from a related technical paper, which is specifically referenced below.

For example, FIG. 7 refers to examples that may be found in Lamba et al., "Hepatic CYP2B6 Expression: Gender and Ethnic Differences and Relationship to CYP2B6 Genotype and CAR (Constitutive Androstane Receptor) Expression," J. Pharm. Exp. Ther., vol. 307:3, pp. 906-22 (December, 2003), which is hereby incorporated by reference in its entirety, and which may be referred to herein as the Lamba reference.

Various forms of the liver enzyme cytochrome p450 function to metabolize agents in the bloodstream, including many clinically important medications. The Lamba reference reports that the liver enzyme cytochrome p450 2B6 ("CYP2B6") activity was 3.6- and 5.0-fold higher in Hispanic females than in Caucasian ($P<0.022$) or African-American females ($P<0.038$). In the Lamba reference, this difference was correlated with single nucleotide polymorphisms ("SNP's"). CYP2B6 is the main enzyme involved in the bioactivation of ifosfamide. Therefore, the effectiveness of ifosfamide may be higher in females (especially Hispanic females) than in males, who generally exhibit a lower CYP2B6 activity than females.

As a hypothetical example, one of the commonly reported adverse events for ifosfamide, an anticancer agent, is darkened and thickened skin. As shown in row 702 of FIG. 7, the study data analysis system 102 could find agents that result in acceptable efficacy of ifosfamide for treating cancer, as described by study efficacy data 306. The study data analysis system 102 could also find data relating to incidence of darkened and thickened skin following ifosfamide administration, as described by study adverse event data 308. The study data analysis system 102 could then identify, for example, a CYP2B6 subpopulation that is characterized by a specific SNP profile and that exhibits a decreased incidence of darkened and thickened skin, as described by subpopulation adverse event data 312. Such a subpopulation could exhibit, for example, at least maintained efficacy following administration of ifosfamide, as described by subpopulation efficacy data 310. Further, the specific SNP CYP2B6 subpopulation may correlate, for example, with Hispanic women between the ages of 20 and 45, as described by subpopulation identifier data 314. It should be noted that the Lamba reference does not disclose the above relationship between study adverse events and CYP2B6 SNP profile, nor a relationship between ethnicity and age. The discussion above on these topics is purely hypothetical and is included merely for illustration purposes.

As another hypothetical example, row 704 of FIG. 7 illustrates an example from McDowell, et al., "Systematic review and meta-analysis of ethnic differences in risks of adverse reactions to drugs used in cardiovascular medicine," Brit. Med. J., vol. 332, pp. 1177-81 (May 5, 2006), which is incorporated by reference in its entirety and which is referred to herein as the McDowell reference.

The McDowell reference analyzed various studies that included at least two ethnic groups and one or more adverse events following administration of cardiovascular medications. Relative risk of an adverse event was calculated for each ethnicity to identify subpopulations at increased risk for an adverse event. Row 704 of FIG. 7 illustrates one example from the McDowell reference in which relative risk of angio-edema following ACE inhibitor administration is the study adverse event data 308, in this case 1 for the combined study population. The subpopulation adverse event data 312 is described in terms of an increased relative risk for angio-edema, in this case 3 for the subpopulation of Black patients. Although not discussed in the McDowell reference, by implication, non-black patients should exhibit a reciprocal, decreased risk for angio-edema.

As a further hypothetical, an analysis of subpopulation adverse event data 312 may result in subpopulation identifier data 314 that further characterizes the subpopulation. For example, an association between the haplotype of the identified Black subpopulation and, for example, the haplotype of individuals of West Indian descent may be identified by the study data analysis system 102. In such an example, the correlation between the two haplotypes comprises subpopulation identifier data 314. It should be noted that the McDowell reference does not disclose the above relationship between the haplotype of the identified Black subpopulation and the haplotype of individuals of West Indian descent. The discussion above on this topic is purely hypothetical and is included merely for illustration purposes.

The McDowell reference did not report efficacy for either the combined study population or the subpopulation, however, this information could be gleaned from the primary references that were the subject of the McDowell reference. In such a case, the study data analysis system 102 could compile, for example, subpopulation efficacy data 310 from one source of study data 106 with subpopulation adverse event data 312 from another source of study data 106 in performing the function of identifying at least one subpopulation having a defined tolerance for at least one adverse event associated with administration of the at least one agent, the at least one subpopulation exhibiting at least some defined level of efficacy upon administration of the at least one agent to the subpopulation.

Figure 8:
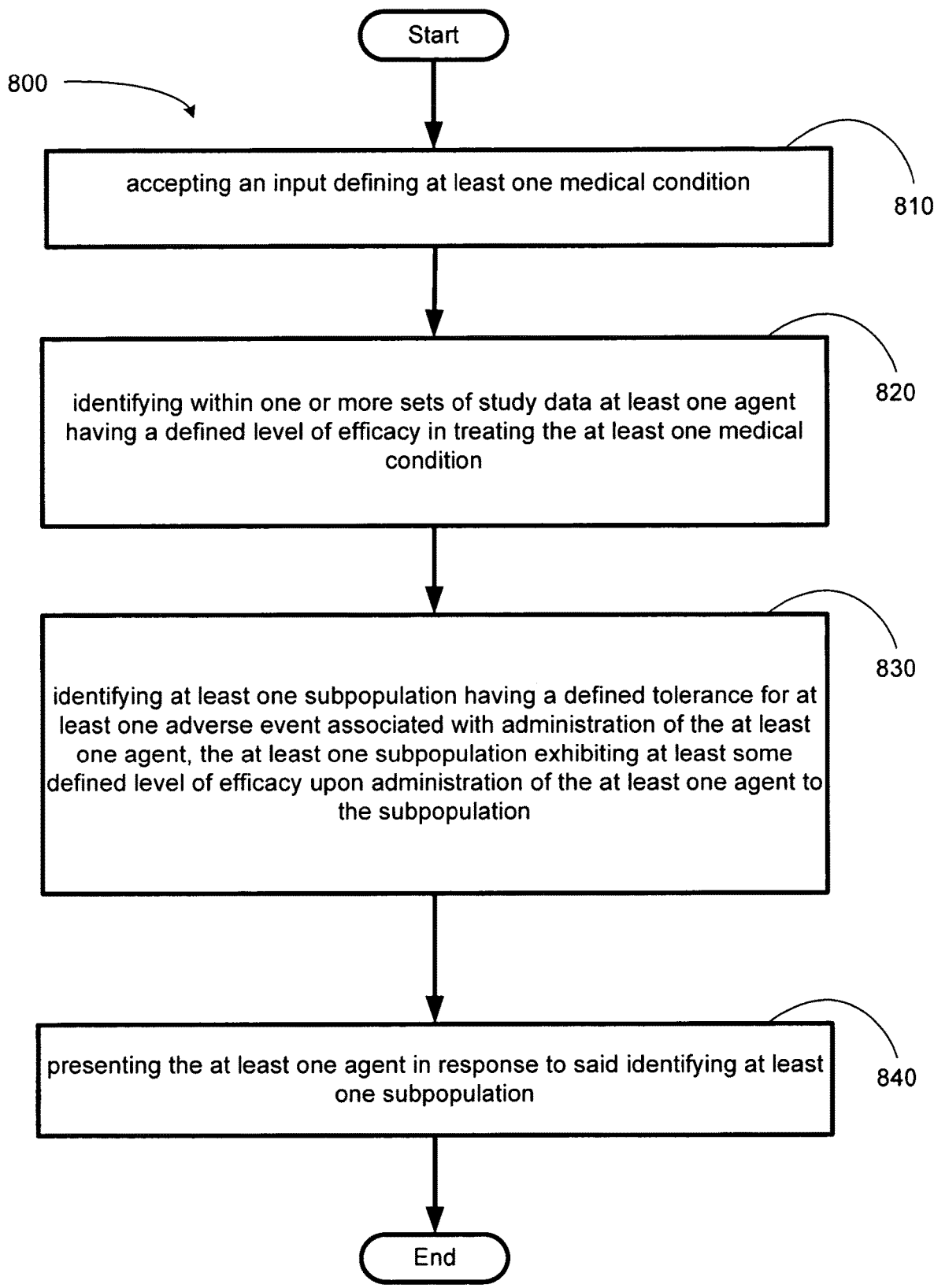
FIG. 8 illustrates an operational flow representing example operations related to medical adverse event data systems.

FIG. 8 illustrates an operational flow 800 representing example operations related to medical adverse event data systems. In FIG. 8 and in following figures that include various examples of operational flows, discussion, and explanation may be provided with respect to the above-described examples of FIGS. 1-7, and/or with respect to other examples and contexts. However, it should be understood that the operational flows may be executed in a number of other environment and contexts, and/or in modified versions of FIGS. 1-7. Also, although the various operational flows are presented in the sequence(s) illustrated, it should be understood that the various operations may be performed in other orders than those which are illustrated, or may be performed concurrently.

After a start operation, operation 810 shows accepting an input defining at least one medical condition. The input may be accepted through a user interface 132 from a clinical researcher 104.

For example, the agent identification logic 126 of the study data analysis system 102 may receive a designation of at least one medical condition, such as, for example, one or more medical indications for which study efficacy data 306 is available. Specifically, this could be a medical indication such as, for example, colon cancer, or a treatment goal such as, for example, reducing wrinkles in the skin.

Operation 820 depicts identifying within one or more sets of study data at least one agent having a defined level of efficacy in treating the at least one medical condition. For example, the agent identification logic 126 of the study data analysis system 102 may identify within a clinical trial database the anti-cancer agent pemetrexed as having at least a 40% partial response rate in treating cancer.

Operation 830 depicts identifying at least one subpopulation having a defined tolerance for at least one adverse event associated with administration of the at least one agent, the at least one subpopulation exhibiting some defined level of efficacy upon administration of the at least one agent to the subpopulation. For example, the subpopulation identification logic 128 of the study data analysis system 102 may identify within a clinical trial database a subpopulation exhibiting a decreased incidence of the adverse event neutropenia and maintained efficacy in treating cancer, following administration of pemetrexed. That subpopulation may be, for example, a set of patients supplemented with folic acid and vitamin B12 prior to treatment with pemetrexed.

Operation 840 illustrates presenting the at least one agent in response to the identification of the at least one subpopulation. For example, the study data analysis system 102 may present an identified agent such as pemetrexed to a clinical researcher 104 via a user interface 132. Optionally, the identified agent(s) and/or identified subpopulation(s) are then assigned to at least one memory. For example, the identified agent(s) and/or identified subpopulation(s) may be assigned to one or more of the various (types of) databases referenced above, such as the relational and/or object-oriented database(s), or to another type of memory, not explicitly mentioned.

In this regard, it should be understood that the identification(s) may first be encoded and/or represented in digital form (i.e., as digital data), prior to the assignment to the at least one memory. For example, a digitally-encoded representation of the identification(s) may be stored in a local memory, or may be transmitted for storage in a remote memory.

Thus, an operation may be performed related either to a local or remote storage of the digital data, or to another type of transmission of the digital data. Of course, as discussed herein, operations also may be performed related to accessing, querying, recalling, or otherwise obtaining the digital data from a memory, including, for example, receiving a transmission of the digital data from a remote memory. Accordingly, such operation(s) may involve elements including at least an operator (e.g., either human or computer) directing the operation, a transmitting computer, and/or a receiving computer, and should be understood to occur within the United States as long as at least one of these elements resides in the United States.

Figure 9:
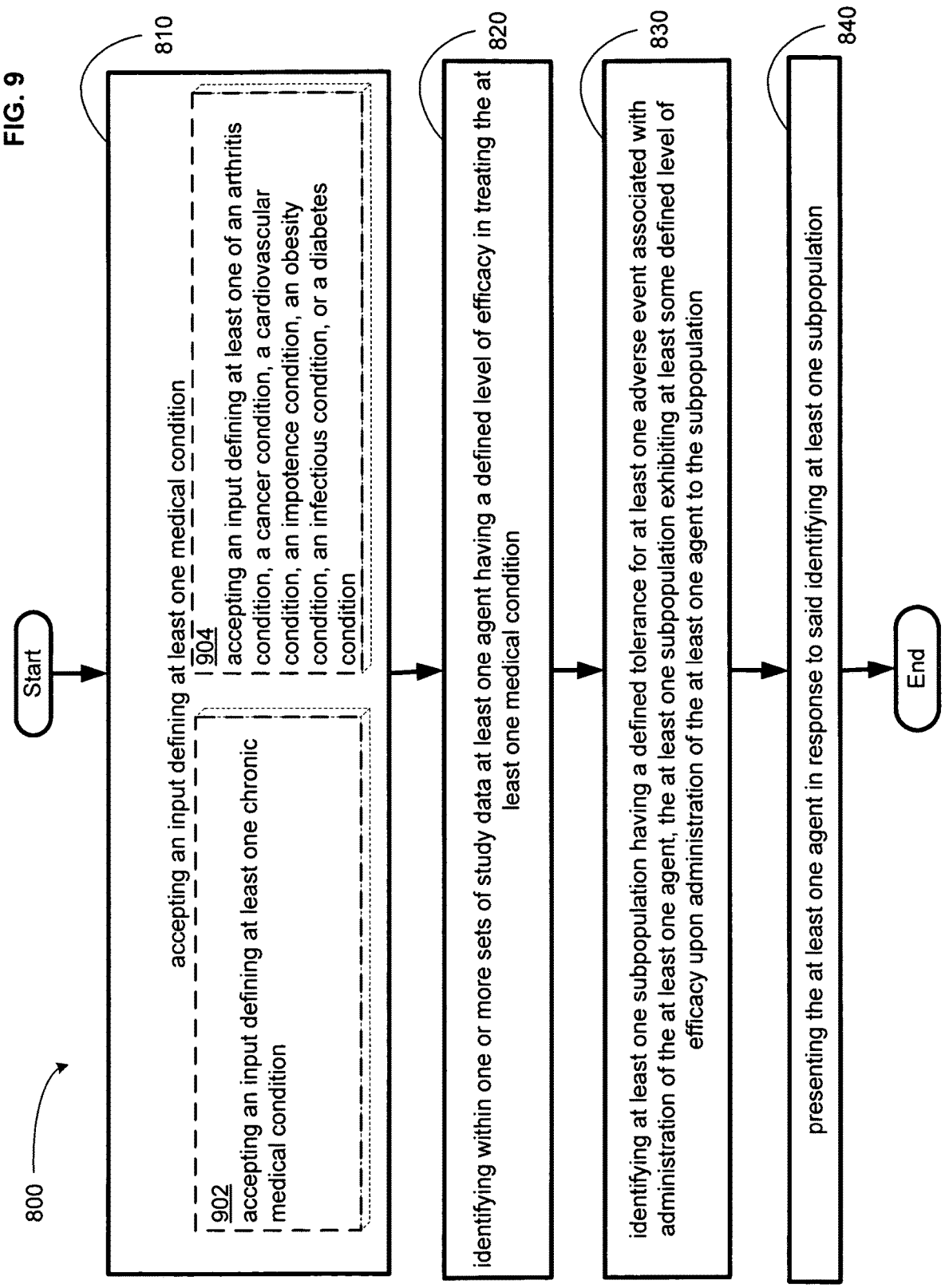
FIG. 9 illustrates an alternative embodiment of the example operational flow of FIG. 8.

FIG. 9 illustrates alternative embodiments of the example operational flow 800 of FIG. 8. FIG. 9 illustrates example embodiments where the defining operation 810 may include at least one additional operation. Additional operations may include operation 902 and/or operation 904.

Operation 902 depicts accepting an input defining at least one chronic medical condition. For example, as referenced herein, the study data analysis system 102 may accept via the user interface 132, for example, a condition that persists over weeks, months or years as the at least one chronic medical condition. The study data analysis system 102 may accept, for example, Acquired Immune Deficiency Syndrome (AIDS) as the at least one chronic medical condition.

Operation 904 depicts accepting an input defining at least one of an arthritis condition, a cancer condition, a cardiovascular condition, an impotence condition, an obesity condition, an infectious condition, or a diabetes condition as the at least one medical condition. For example, the study data analysis system 102 may accept via the user interface 132, for example, a cancer condition such as malignant pleural mesothelioma as the at least one of an arthritis condition, a cancer condition, a cardiovascular condition, an impotence condition, an obesity condition, an infectious condition, or a diabetes condition.

Figure 10:
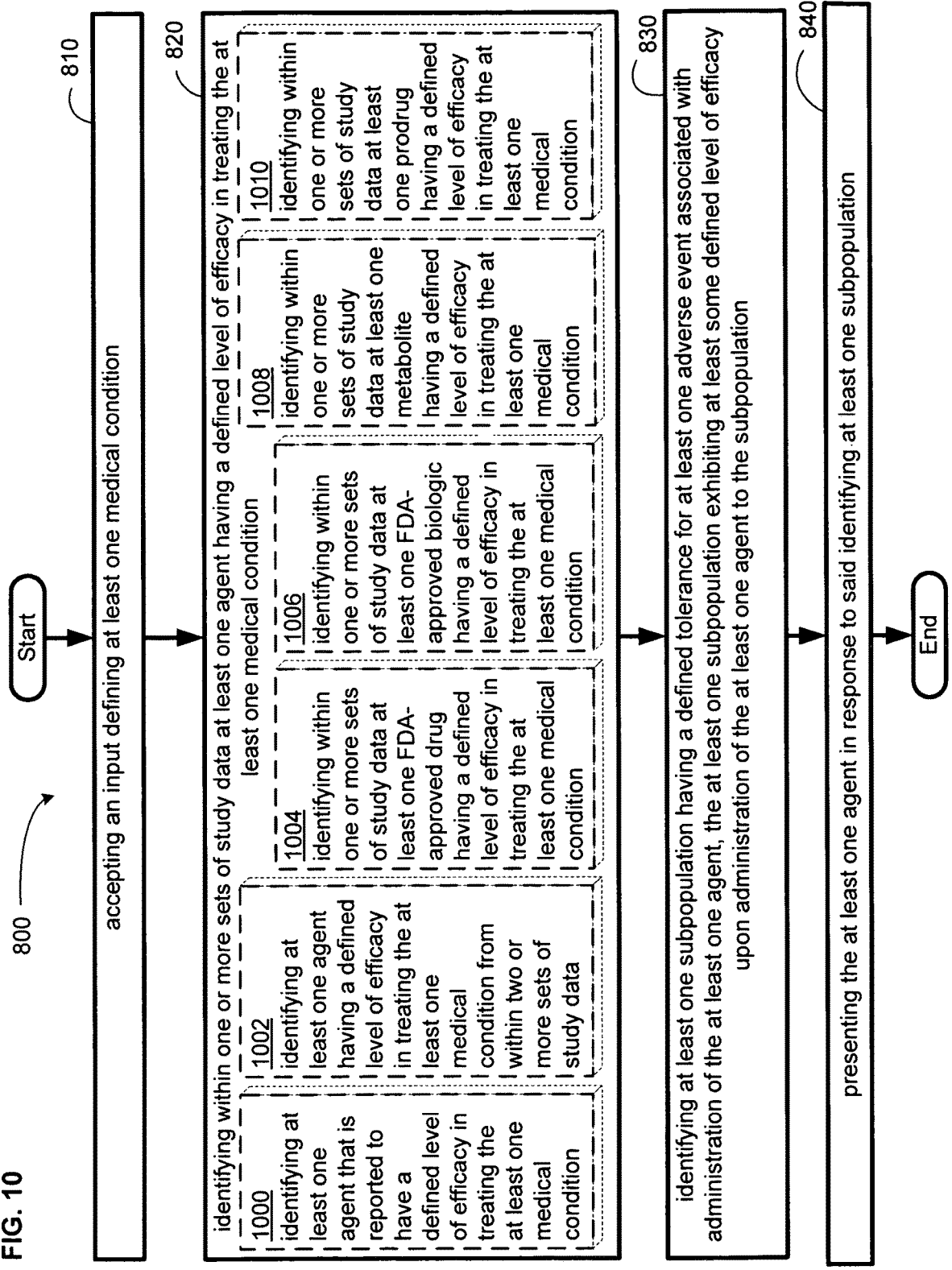
FIG. 10 illustrates an alternative embodiment of the example operational flow of FIG. 8.

FIG. 10 illustrates alternative embodiments of the example operational flow 800 of FIG. 8. FIG. 10 illustrates example embodiments where the identifying operation 820 may include at least one additional operation. Additional operations may include operation 1002, operation 1004, operation 1006, operation 1008, and/or operation 1010.

Operation 1000 depicts identifying at least one agent that is reported to have a defined level of efficacy in treating the at least one medical condition. For example, as shown in row 602 of FIG. 6, efficacy data for pemetrexed combination therapy was reported to be 41.3% compared to 16.7% for cisplatin alone, in the treatment of malignant pleural mesothelioma. These data were reported in the Vogelzang reference. Accordingly, the study data analysis system 102 and/or the agent identification logic 126 may identify pemetrexed as the at least one agent from among the reported Vogelzang efficacy data pertaining to the treatment of malignant pleural mesothelioma, as the at least one medical condition.

Operation 1002 depicts identifying at least one agent having a defined level of efficacy in treating the at least one medical condition from within two or more sets of study data. For example, as shown in row 704 of FIG. 7, study data from more than one set of study data may be used to identify at least one agent having a defined level of efficacy in treating the at least one medical condition. Specifically, for example, the data in row 704 of FIG. 7 are pooled from five studies using a fixed effects model, as reported by the authors of the McDowell reference. Accordingly, the study data analysis system 102 and/or the agent identification logic 126 may combine study data from two or more sets of study data in identifying at least one agent having a defined level of efficacy in treating the at least one medical condition.

Operation 1004 depicts identifying within one or more sets of study data at least one FDA-approved drug having a defined level of efficacy in treating the at least one medical condition. For example, as shown in rows 502 and 504 of FIG. 5, the study data analysis system 102 and/or the agent identification logic 126 may identify the FDA-approved drug Alimta® (pemetrexed) as the at least one agent having a defined level of efficacy in treating the at least one medical condition. Alimta® (pemetrexed) is approved by the FDA for use in treating certain types of cancer.

Operation 1006 shows identifying within one or more sets of study data at least one FDA-approved biologic having a defined level of efficacy in treating the at least one medical condition. For example, the study data analysis system 102 and/or the agent identification logic 126 may identify the FDA-approved biologic Neupogen® as the at least one agent having a defined level of efficacy in treating the at least one medical condition. Neupogen® is approved by the FDA for, inter alia, reducing the time to neutrophil recovery and the duration of fever, following induction or consolidation chemotherapy treatment of adults with acute myeloid leukemia.

Operation 1008 shows identifying within one or more sets of study data at least one metabolite having a defined level of efficacy in treating the at least one medical condition. For example, the study data analysis system 102 and/or the agent identification logic 126 may identify metabolites of pemetrexed, including polyglutamated pemetrexed, as the at least one agent having a defined level of efficacy in treating the at least one medical condition. Polyglutamated pemetrexed is the active intracellular metabolite of pemetrexed, which is effective in the treatment of, inter alia, malignant pleural mesothelioma which is unresectable or in patients who are otherwise not candidates for curative surgery.

Operation 1010 shows identifying within one or more sets of study data at least one prodrug having a defined level of efficacy in treating the at least one medical condition. For example, the study data analysis system 102 and/or the agent identification logic 126 may identify the amprenavir prodrug Lexiva® as the at least one agent having a defined level of efficacy in treating the at least one medical condition. Lexiva® is effective in the treatment of HIV infection in adults in combination with other antiretroviral agents.

Figure 11:
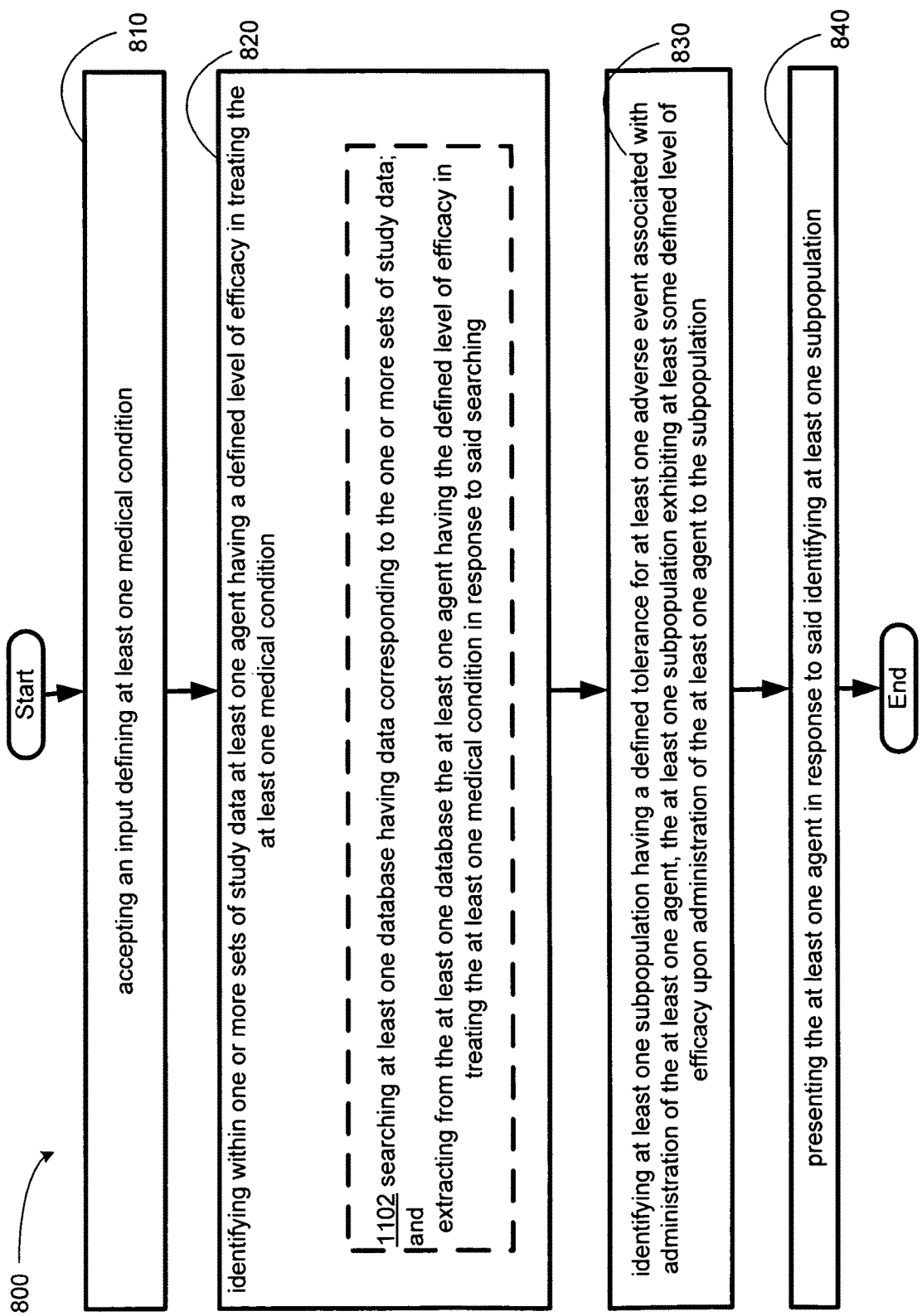
FIG. 11 illustrates an alternative embodiment of the example operational flow of FIG. 8.

FIG. 11 illustrates alternative embodiments of the example operational flow 800 of FIG. 8. FIG. 11 illustrates example embodiments where the defining operation 820 may include at least one additional operation. Additional operations may include operation 1102.

Operation 1102 shows searching at least one database having data corresponding to the one or more sets of study data; and extracting from the at least one database the at least one agent having the defined level of efficacy in treating the at least one medical condition in response to said searching. For example, the study data analysis system 102 and/or the agent identification logic 126 may search at least one database having study efficacy data 306 and/or study adverse event data 308. The study data analysis system 102 and/or the agent identification logic 126 may then extract from the at least one database at least one agent having a defined level of efficacy in treating the at least one medical condition in response to said searching. For example, the study data analysis system 102 and/or the agent identification logic 126 may search the PubMed database for agents that are effective in treating malignant pleural mesothelioma, and the study data analysis system 102 and/or the agent identification logic 126 may then extract from the PubMed database pemetrexed, which, as discussed above, is effective in treating malignant pleural mesothelioma.

Figure 12:
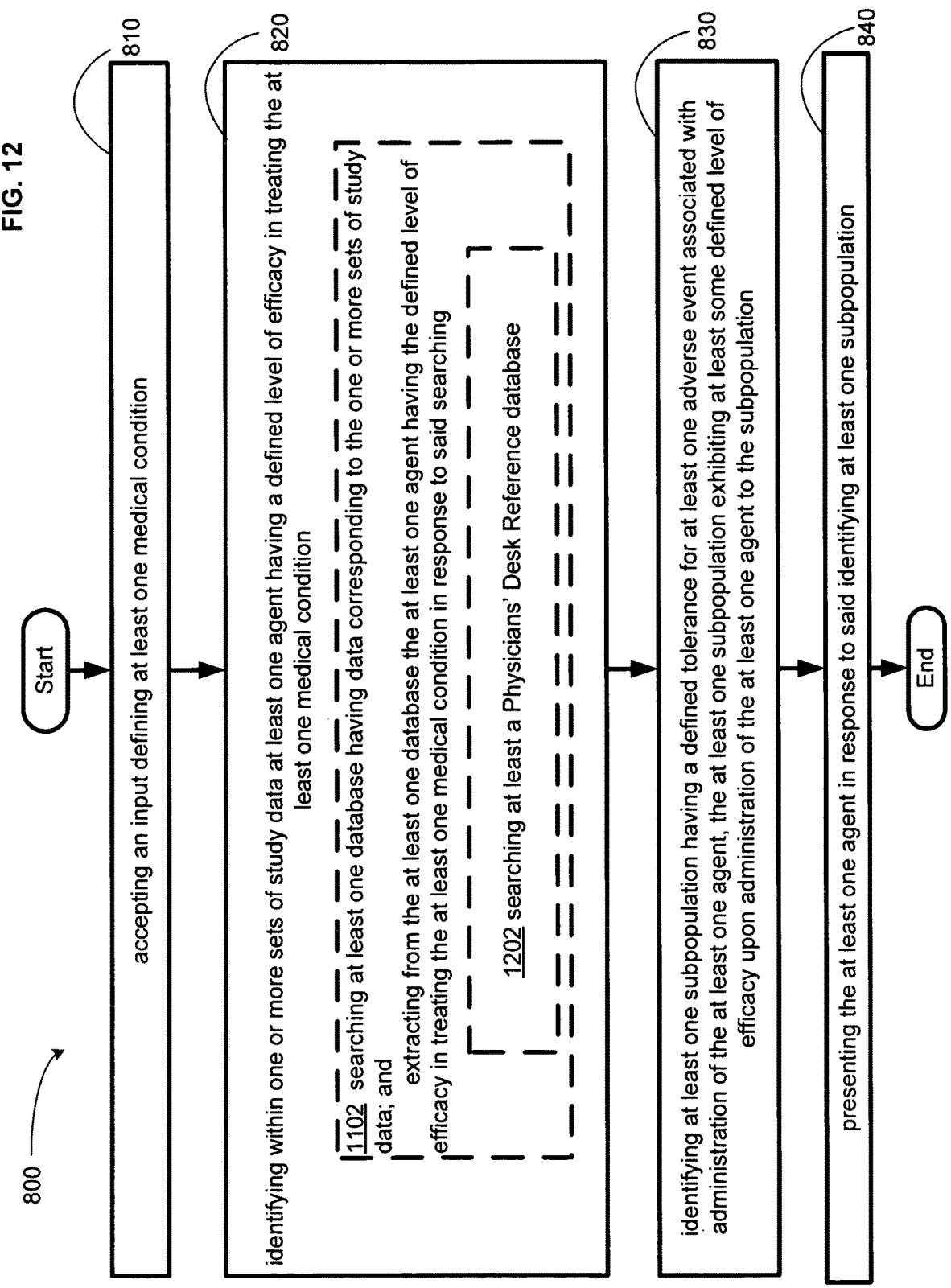
FIG. 12 illustrates an alternative embodiment of the example operational flow of FIG. 8.

FIG. 12 illustrates alternative embodiments of the example operational flow 800 of FIG. 11. FIG. 12 illustrates example embodiments where the defining operation 1102 may include at least one additional operation. Additional operations may include operation 1202.

Operation 1202 shows searching at least a Physicians' Desk Reference database in the context of operation 1102 searching at least one database having data corresponding to the one or more sets of study data; and extracting from the at least one database the at least one agent having the defined level of efficacy in treating the at least one medical condition in response to said searching. For example, the study data analysis system 102 and/or the agent identification logic 126 may search the PDRhealth clinical trials database for an agent having a defined level of efficacy in treating pain, and the study data analysis system 102 and/or the agent identification logic 126 may extract oxycodone as the at least one agent having a defined level of efficacy in treating the at least one medical condition (e.g., pain) in response to said searching.

Figure 13:
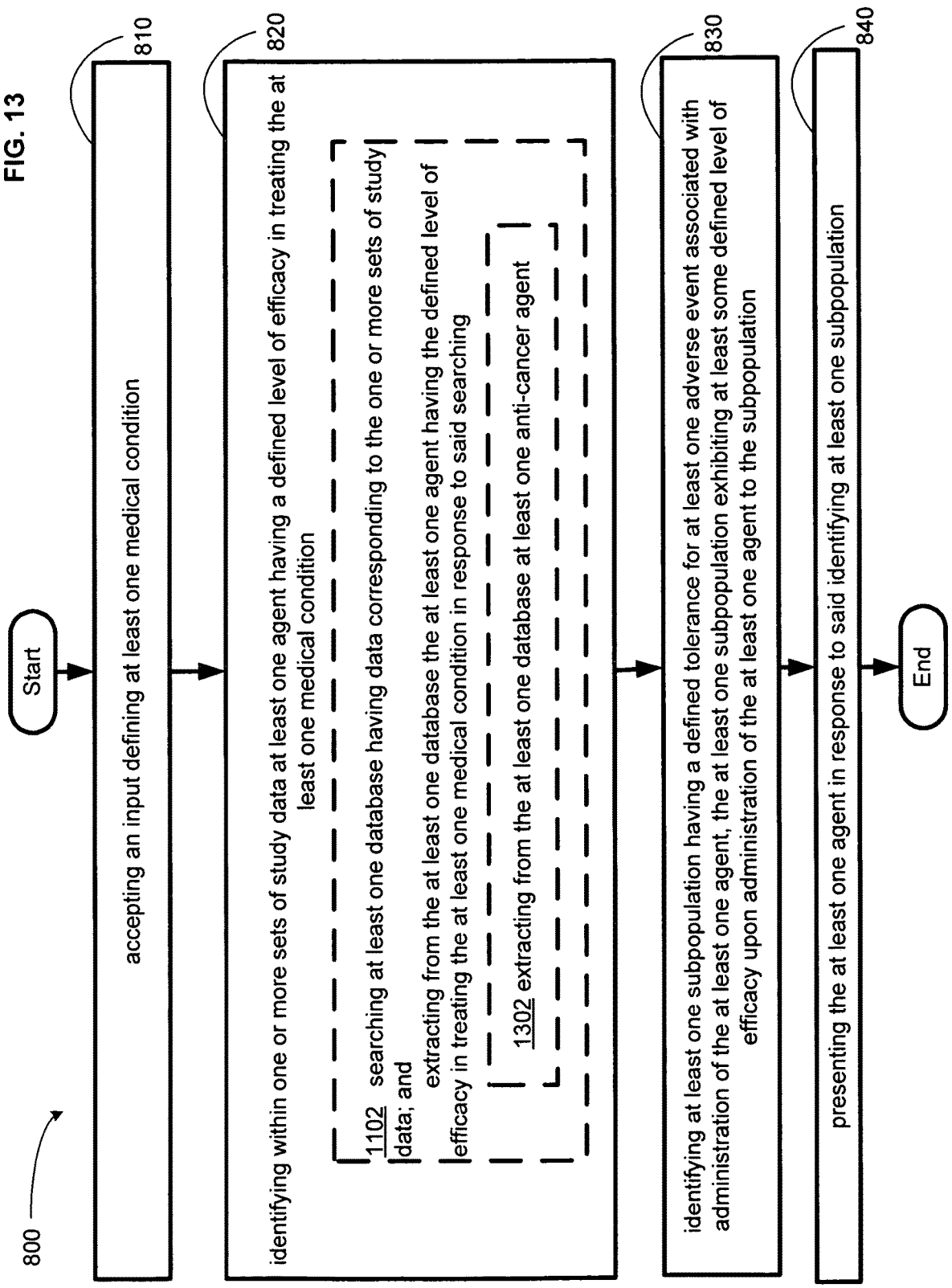
FIG. 13 illustrates an alternative embodiment of the example operational flow of FIG. 8.

FIG. 13 illustrates alternative embodiments of the example operational flow 800 of FIG. 8. FIG. 13 illustrates example embodiments where the defining operation 1102 may include at least one additional operation. Additional operations may include operation 1302.

Operation 1302 shows extracting from the at least one database at least one anti-cancer agent in the context of operation 1102 searching at least one database having data corresponding to the one or more sets of study data; and extracting from the at least one database the at least one agent having the defined level of efficacy in treating the at least one medical condition in response to said searching. For example, the study data analysis system 102 and/or the agent identification logic 126 may search the National Cancer Institute's PDQ® comprehensive cancer database. The study data analysis system 102 and/or the agent identification logic 126 may then, for example, in response to accepting an input defining osteosarcoma as the at least one medical condition, search the PDQ® comprehensive cancer database for agents with efficacy in treating osteosarcoma, and then extract one or more agents, such as, for example, ifosfamide. Ifosfamide is medically indicated for the treatment of osteosarcoma.

Figure 14:
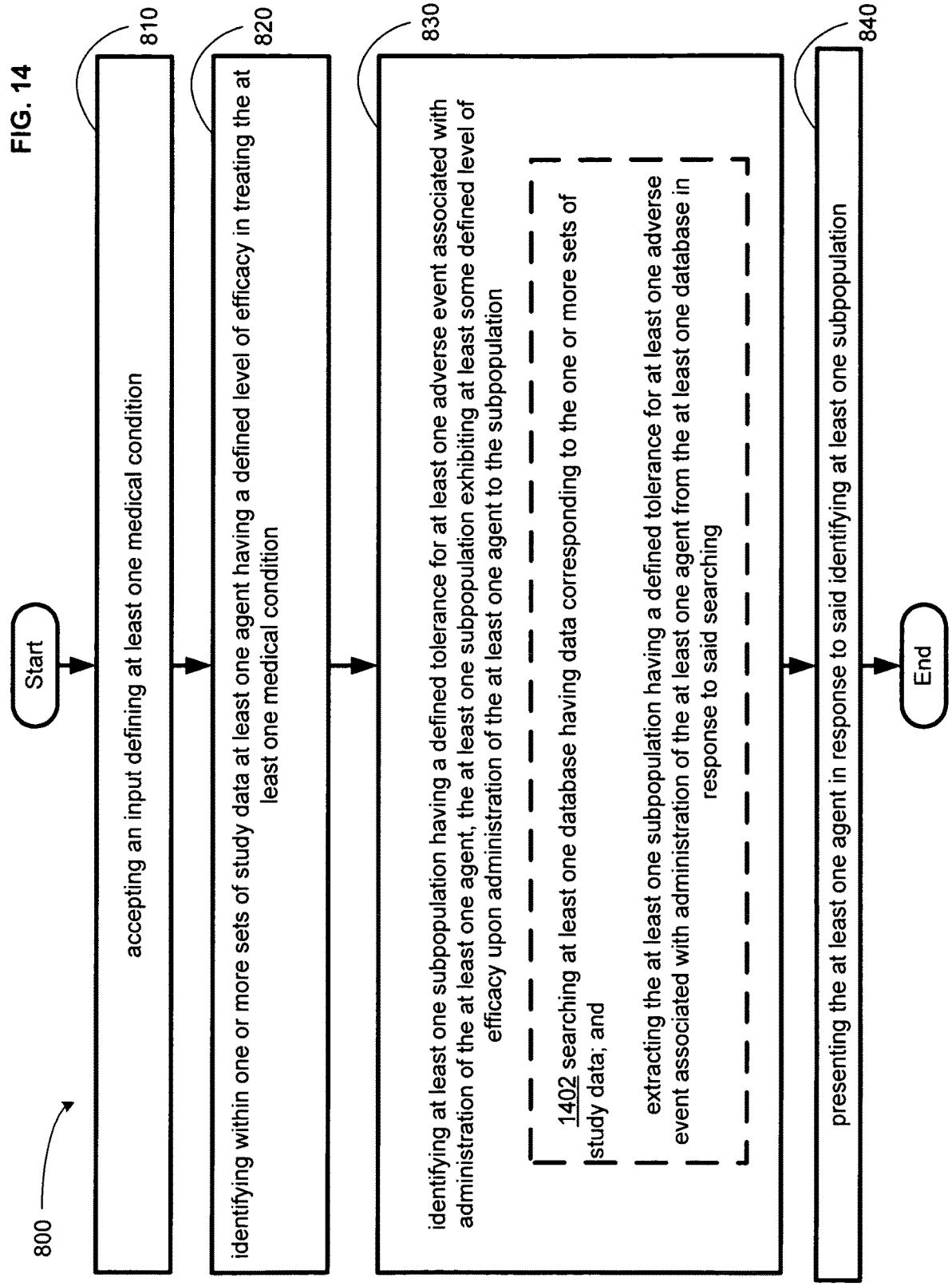
FIG. 14 illustrates an alternative embodiment of the example operational flow of FIG. 8.

FIG. 14 illustrates alternative embodiments of the example operational flow 800 of FIG. 8. FIG. 14 illustrates example embodiments where the defining operation 830 may include at least one additional operation. Additional operations may include operation 1402.

Operation 1402 shows searching at least one database having data corresponding to the one or more sets of study data; and extracting the at least one subpopulation having a defined tolerance for at least one adverse event associated with administration of the at least one agent from the at least one database in response to said searching, in the context of operation 830. For example, the study data analysis system 102 and/or the subpopulation identification logic 128 may search the http://www.clinicaltrialresults.org database for subpopulations that tolerate pemetrexed for the treatment of malignant pleural mesothelioma, in terms of the adverse event neutropenia, and which subpopulations experience adequate efficacy in terms of tumor response rate. Such data is available on a webpage that describes a clinical trial conducted by Eli Lilly and Company entitled "A Single-blind Randomized Phase 3 Trial of ALIMTA (pemetrexed) plus Cisplatin versus Cisplatin Alone in Patients with Malignant Pleural Mesothelioma." This is the clinical trial that generated the data described in FIG. 6, rows 602, 604 and 606. The study data analysis system 102 and/or the subpopulation identification logic 128 may then extract the subpopulation of patients supplemented with folic acid and vitamin B12 as one that experiences less neutropenia and adequate efficacy in terms of, for example, tumor response rate.

Figure 15:
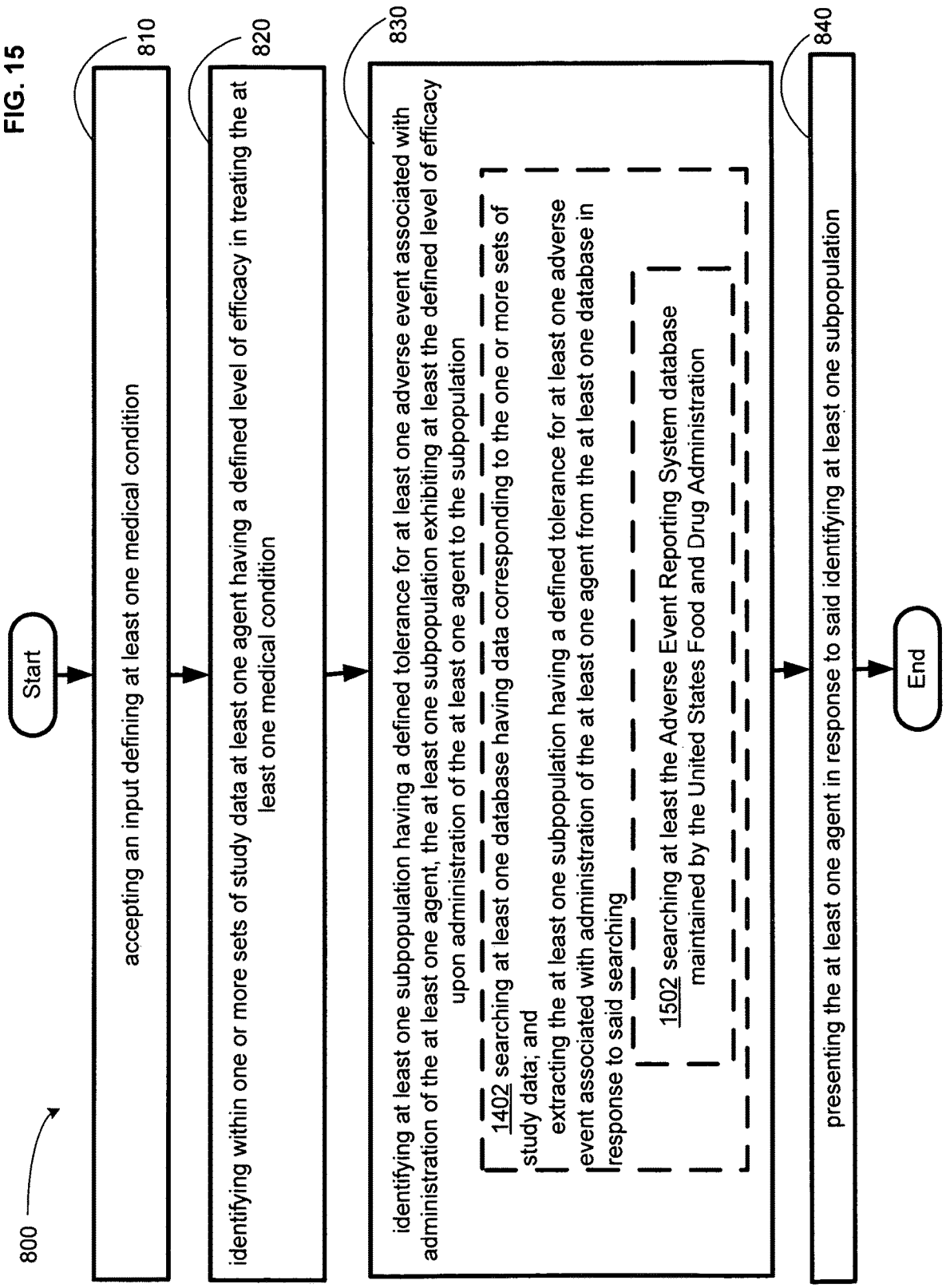
FIG. 15 illustrates an alternative embodiment of the example operational flow of FIG. 8.

FIG. 15 illustrates alternative embodiments of the example operational flow 800 of FIG. 8. FIG. 15 illustrates example embodiments where the defining operation 830 may include at least one additional operation. Additional operations may include operation 1502.

Operation 1502 shows searching at least the Adverse Event Reporting System database maintained by the United States Food and Drug Administration, in the context of operation 1402. For example, the study data analysis system 102 and/or the subpopulation identification logic 128 may search at least the Adverse Event Reporting System database maintained by the United States Food and Drug Administration for "malignant pleural mesothelioma" to identify the subpopulation supplemented with folic acid and vitamin B12 as experiencing decreased neutropenia and maintained efficacy. The supplemented subpopulation may then be extracted by the study data analysis system 102 and/or the subpopulation identification logic 128.

FIG. 16 illustrates alternative embodiments of the example operational flow 800 of FIG. 8. FIG. 16 illustrates example embodiments where the defining operation 830 may include at least one additional operation. Additional operations may include operation 1602, operation 1604, operation 1606, operation 1608, operation 1610, operation 1612, operation 1614, operation 1616, operation 1618, and/or operation 1620.

Operation 1602 shows extracting from the at least one database a subpopulation characterized by one or more genetic parameters, in the context of operation 1402. For example, the study data analysis system 102 and/or the subpopulation identification logic 128 may extract a subpopulation characterized by individual DNA sequence.

Operation 1604 shows extracting from the at least one database a subpopulation characterized by one or more epigenetic parameters, in the context of operation 1402. For example, the study data analysis system 102 and/or the subpopulation identification logic 128 may extract a subpopulation characterized by DNA methylation data.

Operation 1606 shows extracting from the at least one database a subpopulation characterized by one or more biochemical parameters, in the context of operation 1402. For example, the study data analysis system 102 and/or the subpopulation identification logic 128 may extract one or more subpopulations characterized by cytochrome p450 activity data.

Operation 1608 shows extracting from the at least one database a subpopulation characterized by one or more gene expression parameters, in the context of operation 1402. For example, the study data analysis system 102 and/or the subpopulation identification logic 128 may extract one or more subpopulations characterized by low affinity neurotrophin receptor mRNA expression data.

Operation 1610 shows extracting from the at least one database a subpopulation characterized by one or more protein expression parameters, in the context of operation 1402. For example, the study data analysis system 102 and/or the subpopulation identification logic 128 may extract one or more subpopulations characterized by interferon gamma protein level data.

Operation 1612 shows extracting from the at least one database a subpopulation characterized by one or more behavioral parameters, in the context of operation 1402. For example, the study data analysis system 102 and/or the subpopulation identification logic 128 may extract one or more subpopulations characterized by smoking and/or non-smoking behavior data.

Operation 1614 shows extracting from the at least one database a subpopulation characterized by one or more physiologic parameters, in the context of operation 1402. For example, the study data analysis system 102 and/or the subpopulation identification logic 128 may extract one or more subpopulations characterized by blood pressure, respiration, and/or pulmonary vascular resistance data.

Operation 1616 shows extracting from the at least one database a subpopulation characterized by one or more demographic parameters, in the context of operation 1402. For example, the study data analysis system 102 and/or the subpopulation identification logic 128 may extract one or more subpopulations characterized by geographical origin, gender, age, ethnicity and/or race data.

Operation 1617 shows extracting from the at least one database a subpopulation characterized by one or more of age, gender, ethnicity, race, liver enzyme genotype, or medical history. For example, the study data analysis system 102 and/or the subpopulation identification logic 128 may extract one or more subpopulations that share a common national origin, age group, cytochrome p450 makeup, and/or, for example, history of diabetes.

Operation 1618 shows extracting from the at least one database a subpopulation characterized by one or more of lifestyle, exercise regimen, diet, nutritional regimen, dietary supplementation, concomitant medical therapy, or concomitant alternative medical therapy, in the context of operation 1402. For example, the study data analysis system 102 and/or the subpopulation identification logic 128 may extract one or more subpopulations characterized by body weight, vitamin intake, nutraceutical intake, and/or acupuncture regimen data.

Operation 1620 shows extracting from the at least one database a subpopulation characterized by one or more of linkage disequilibrium analysis profile, haplotype profile, single nucleotide polymorphism profile, or individual genetic sequence profile, in the context of operation 1402. For example, the study data analysis system 102 and/or the subpopulation identification logic 128 may extract one or more subpopulations characterized by DNA mutation and/or variation data.

Operation 1622 shows extracting from the at least one database a subpopulation having a significantly lower incidence of at least one adverse event than that of at least one reported clinical trial for the at least one agent, in the context of operation 1402. For example, as described in FIG. 5, row 2, the study data analysis system 102 and/or subpopulation identification logic 128 may extract one or more subpopulations that has a significantly lower incidence of angio-edema than the incidence of angio-edema in at least one reported clinical trial for at least one angiotensin converting enzyme inhibitor.

Figure 17:
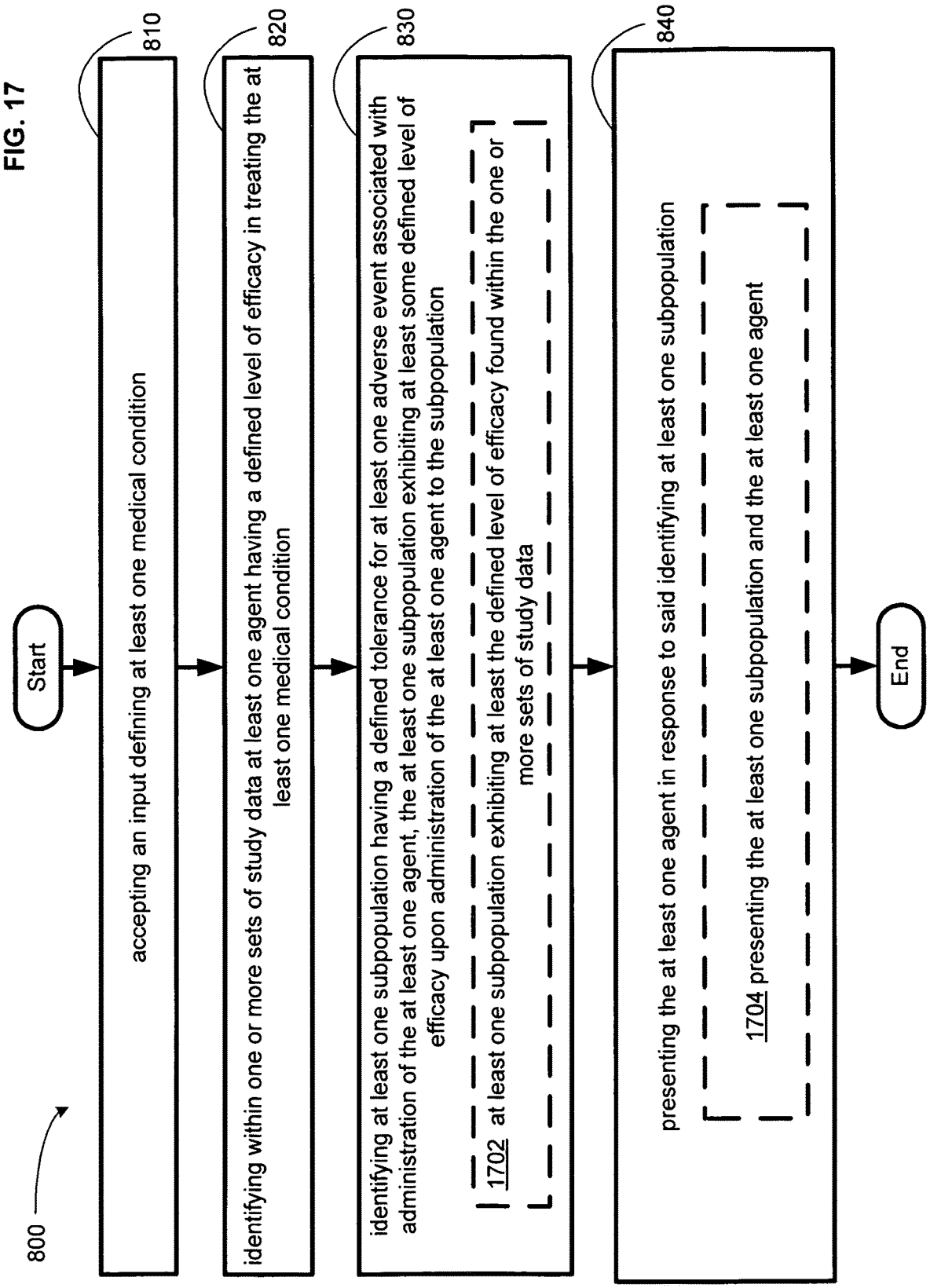
FIG. 17 illustrates an alternative embodiment of the example operational flow of FIG. 8.

FIG. 17 illustrates alternative embodiments of the example operational flow 800 of FIG. 8. FIG. 17 illustrates example embodiments where the presenting operation 840 may include at least one additional operation. Additional operations may include operation 1702, and/or operation 1704.

Operation 1702 shows at least one subpopulation exhibiting at least the defined level of efficacy found within the one or more sets of study data, as the subpopulation exhibiting at least some defined level of efficacy upon administration of the at least one agent to the subpopulation, in the context of operation 830. For example, as shown in row 602 of FIG. 6, pemetrexed/cisplatin exhibits a 45.6% partial response rate compared to 19% for cisplatin alone in the supplemented subpopulation. This efficacy measure for the subpopulation is at least as high as the efficacy measure for the overall population in the set of study data presented in the Vogelzang reference (i.e., 41.3% partial response rate for pemetrexed/cisplatin compared to 16.7% for cisplatin alone). Accordingly, if the defined level of efficacy is the 41.3% partial response level of efficacy of the overall population of the Vogelzang reference, then the supplemented subpopulation of the Vogelzang reference exhibits at least the defined level of efficacy (i.e., 45.6% partial response). Accordingly, the study data analysis system 102 and/or subpopulation identification logic 128 may, for example, identify a folate/vitamin B12-supplemented population as the at least one subpopulation exhibiting at least the defined level of efficacy found within the one or more sets of study data.

Operation 1704 shows presenting the at least one subpopulation and the at least one agent, in the context of operation 840. For example, if the study data analysis system 102 and/or agent identification logic 126 and/or subpopulation identification logic 128 identifies aspirin as the agent for which administration to an ethnic subpopulation results in a defined decrease of an adverse event, while maintaining efficacy, the study data analysis system 102 and/or user interface 132 and/or user interface 208 may present both the agent, aspirin, and the ethnic subpopulation to the clinical researcher 104.

Figure 18:
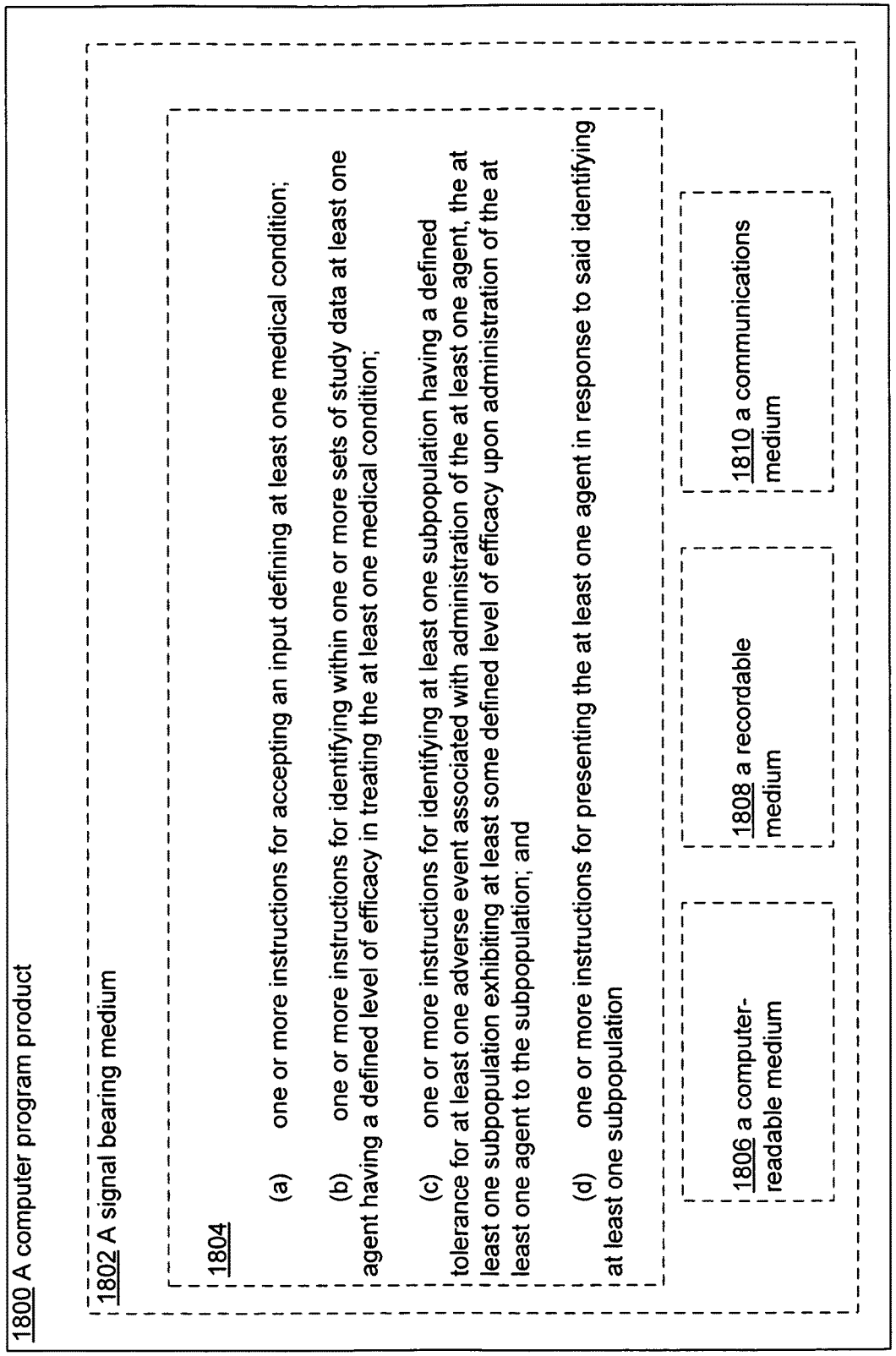
FIG. 18 illustrates a partial view of an example computer program product that includes a computer program for executing a computer process on a computing device.

FIG. 18 illustrates a partial view of an example computer program product 1800 that includes a computer program 1804 for executing a computer process on a computing device. An embodiment of the example computer program product 1800 is provided using a signal bearing medium 1802, and may include at one or more instructions for accepting an input defining at least one medical condition; one or more instructions for identifying within one or more sets of study data at least one agent having a defined level of efficacy in treating the at least one medical condition; one or more instructions for identifying at least one subpopulation having a defined tolerance for at least one adverse event associated with administration of the at least one agent, the at least one subpopulation exhibiting at least some defined level of efficacy upon administration of the at least one agent to the subpopulation; and one or more instructions for presenting the at least one agent in response to said identifying at least one subpopulation. The one or more instructions may be, for example, computer executable and/or logic-implemented instructions. In one implementation, the signal-bearing medium 1802 may include a computer-readable medium 1806. In one implementation, the signal bearing medium 1802 may include a recordable medium 1808. In one implementation, the signal bearing medium 1802 may include a communications medium 1810.

Figure 19:
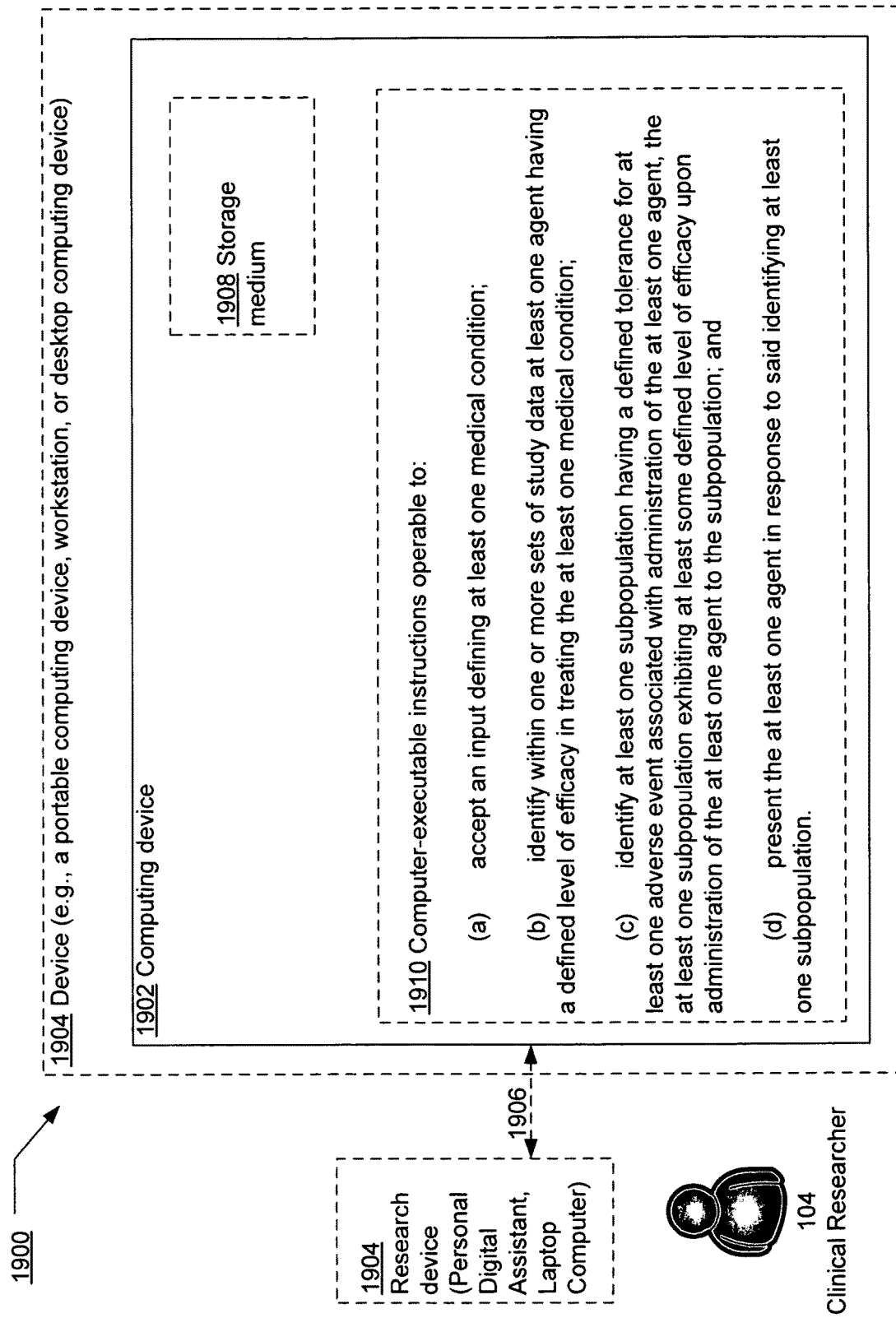
FIG. 19 illustrates an example device in which embodiments may be implemented.

FIG. 19 illustrates an example system 1900 in which embodiments may be implemented. The system 1900 includes a computing system environment. The system 1900 also illustrates the clinical researcher 104 using a device 1904, which is optionally shown as being in communication with a computing device 1902 by way of an optional coupling 1906. The optional coupling 1906 may represent a local, wide-area, or peer-to-peer network, or may represent a bus that is internal to a computing device (e.g., in example embodiments in which the computing device 1902 is contained in whole or in part within the device 1904). A storage medium 1908 may be any computer storage media.

The computing device 1902 includes computer-executable instructions 1910 that when executed on the computing device 1902 cause the computing device 1902 to accept an input defining at least one medical condition; to identify within one or more sets of study data at least one agent having a defined level of efficacy in treating the at least one medical condition; to identify at least one subpopulation having a defined tolerance for at least one adverse event associated with administration of the at least one agent, the at least one subpopulation exhibiting at least some defined level of efficacy upon administration of the at least one agent to the subpopulation; and to present the at least one agent in response to said identifying of at least one subpopulation. As referenced above and as shown in FIG. 19, in some examples, the computing device 1902 may optionally be contained in whole or in part within the research device 1904.

In FIG. 19, then, the system 1900 includes at least one computing device (e.g., 1902 and/or 1904). The computer-executable instructions 1910 may be executed on one or more of the at least one computing device. For example, the computing device 1902 may implement the computer-executable instructions 1910 and output a result to (and/or receive data from) the computing (research) device 1904. Since the computing device 1902 may be wholly or partially contained within the computing (research) device 1904, the research device 1904 also may be said to execute some or all of the computer-executable instructions 1910, in order to be caused to perform or implement, for example, various ones of the techniques described herein, or other techniques.

The research device 1904 may include, for example, a portable computing device, workstation, or desktop computing device. In another example embodiment, the computing device 1902 is operable to communicate with the clinician device 1904 associated with the clinical researcher 104 to receive information about the input from the clinical researcher 104 for performing the identifications and presenting the at least one agent.

FIG. 20 illustrates alternative embodiments of the example operational flow 800 of FIG. 8. FIG. 20 illustrates example embodiments where an additional operation precedes the presenting operation 840, and the presenting operation 840 may include at least one additional operation. Additional operations may include operation 2036 and 2040.

Operation 2036 shows correlating the at least one subpopulation with subpopulation identifier data, directly after operation 830. For example, if the study data analysis system 102 has identified aspirin as an agent for which administration to a subpopulation characterized by, for example, a particular cytokine RNA expression profile, results in a specified decrease of an adverse event, while maintaining efficacy, the study data analysis system 102 and/or subpopulation identification logic 128 may then correlate the cytokine RNA expression profile with a specific, distinguishing clinical population. For example, the cytokine RNA expression profile of Native Americans may match the particular cytokine RNA expression profile identified for aspirin.

Operation 2040 shows presenting the at least one agent and the subpopulation identifier data, in the context of operation 840. For example, if the study data analysis system 102 and/or subpopulation identification logic 128 has identified aspirin as an agent that results in a specified decrease of an adverse event in Native Americans, while maintaining efficacy, the study data analysis system 102 and/or subpopulation identification logic 128 may present both the agent, aspirin, and the subpopulation identifier data 314, i.e, the Native American cytokine RNA expression profile.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected," or "operably coupled," to each other to achieve the desired functionality. Any two components capable of being so associated can also be viewed as being "operably couplable" to each other to achieve the desired functionality. Specific examples of operably couplable include but are not limited to physically mateable and/or physically interacting components and/or wirelessly interactable and/or wirelessly interacting components and/or logically interacting and/or logically interactable components.

While certain features of the described implementations have been illustrated as disclosed herein, many modifications, substitutions, changes and equivalents will now occur to those skilled in the art. It is, therefore, to be understood that the appended claims are intended to cover all such modifications and changes as fall within the true spirit of the embodiments of the invention.

While particular aspects of the present subject matter described herein have been shown and described, it will be apparent to those skilled in the art that, based upon the teachings herein, changes and modifications may be made without departing from this subject matter described herein and its broader aspects and, therefore, the appended claims are to encompass within their scope all such changes and modifications as are within the true spirit and scope of this subject matter described herein. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A system comprising:
    circuitry for accepting an input indicating a cancer condition associated with a patient;
    circuitry for identifying an anti-cancer agent having a defined level of efficacy in treating the cancer condition;
    circuitry for obtaining a sample from the patient;
    circuitry for analyzing the sample obtained from the patient to determine whether the patient is within at least one subpopulation based on at least one of gene expression data, protein expression data, or metabolite data determined from the sample;
    circuitry for determining an alternative medical intervention for administration in association with the anti-cancer agent based at least partly on the at least one of gene expression data, protein expression data, or metabolite data determined from the sample that at least partially improves the defined level of efficacy in treating the cancer condition; and
    circuitry for displaying a treatment regimen for the anti-cancer agent and the alternative medical intervention for treating the cancer condition.

2. The system of claim 1, wherein the circuitry for accepting an input indicating a cancer condition associated with a patient comprises:
    circuitry for accepting an input indicating a cancer condition along with at least one of a chronic medical condition, an arthritis condition, a cardiovascular condition, an impotence condition, an obesity condition, an infectious condition, or a diabetes condition.

3. The system of claim 1, wherein the circuitry for determining an alternative medical intervention for administration in association with the anti-cancer agent based at least partly on the at least one of gene expression data, protein expression data, or metabolite data determined from the sample that at least partially improves the defined level of efficacy in treating the cancer condition comprises:
circuitry for determining at least one of a biologic, nutraceutical, or dietary supplemental agent for administration in association with the anti-cancer agent based at least partly on at least one indication of a mitigating effect on at least one adverse event associated with the anti-cancer agent when the anti-cancer agent is co-administered with the at least one of the biologic, nutraceutical, or dietary supplemental agent, and
wherein the circuitry for displaying a treatment regimen for the anti-cancer agent and the alternative medical intervention for treating the cancer condition includes at least:
circuitry for displaying a dosing schedule for the anti-cancer agent, the at least one biologic, nutraceutical, or dietary supplemental agent, and for presenting the decreased incidence level associated with the at least one biologic, nutraceutical, or dietary supplemental agent.

4. The system of claim 3, wherein the circuitry for determining an alternative medical intervention for administration in association with the anti-cancer agent based at least partly on the at least one of gene expression data, protein expression data, or metabolite data determined from the sample that at least partially improves the defined level of efficacy in treating the cancer condition comprises:
circuitry for determining at least one subpopulation that self reports a less severe at least one adverse event than that of at least one reported clinical trial for the anti-cancer agent; and
circuitry for determining whether the at least one subpopulation associated with the less severe at least one adverse event was administered the alternative medical intervention.

5. The system of claim 1, further comprising:
circuitry for detecting at least one indication of a reduced efficacy of the anti-cancer agent responsive to administration of the alternative medical intervention.

6. The system of claim 1, further comprising:
circuitry for detecting at least one indication of an improved efficacy of the anti-cancer agent responsive to administration of the alternative medical intervention.

7. The system of claim 1, wherein the circuitry for analyzing the sample obtained from the patient to determine whether the patient is within at least one subpopulation based on at least one of gene expression data, protein expression data, or metabolite data determined from the sample comprises:
circuitry for determining whether the patient is exhibiting one or more symptoms associated with at least one adverse event, the at least one adverse event associated with the anti-cancer agent.

8. The system of claim 1, wherein the sample comprises one or more of a tissue sample from the patient or a gastrointestinal tract sample from the patient.

9. The system of claim 8, wherein the wherein the tissue sample comprises one or more of a blood sample or a plasma sample.

10. The system of claim 1, further comprising circuitry for characterizing a treatment goal associated with the patient based on the obtained at least one of gene expression data, protein expression data, or metabolite data; and
wherein the circuitry for determining an alternative medical intervention for administration in association with the anti-cancer agent based at least partly on the at least one of gene expression data, protein expression data, or metabolite data determined from the sample that at least partially improves the defined level of efficacy in treating the cancer condition comprises:
circuitry for determining an alternative medical intervention for administration in association with the anti-cancer agent based at least partly on the at least one of gene expression data, protein expression data, or metabolite data determined from the sample that at least partially improves the defined level of efficacy and at least partially promotes the treatment goal.

11. The system of claim 10, further comprising circuitry for associating a subpopulation identifier with the patient based at least partly on the at least one of gene expression data, protein expression data, or metabolite data from the sample.

12. The system of claim 11, wherein the subpopulation identifier informs the characterizing a treatment goal associated with the patient.

13. The system of claim 1, wherein the circuitry for determining an alternative medical intervention for administration in association with the anti-cancer agent based at least partly on the at least one of gene expression data, protein expression data, or metabolite data determined from the sample that at least partially improves the defined level of efficacy in treating the cancer condition comprises:
circuitry for querying a genomic DNA database to identify a subpopulation having a DNA sequence associated with the defined level of efficacy, and
circuitry for determining whether the patient's at least one of gene expression data, protein expression data, or metabolite data includes the specific DNA sequence associated with the defined level of efficacy.

14. The system of claim 1, further comprising:
circuitry for determining whether the patient is exhibiting one or more symptoms associated with an adverse event.

15. The system of claim 1, wherein the circuitry for analyzing the sample obtained from the patient to determine whether the patient is within at least one subpopulation based on at least one of gene expression data, protein expression data, or metabolite data determined from the sample comprises:
circuitry for confirming the level of efficacy of the anti-cancer agent in the patient based on the gene expression data, protein expression data, or metabolite data.

16. A computer program product comprising:
a non-transitory computer-readable medium bearing instructions including at least:
one or more instructions for accepting an input indicating a cancer condition associated with a patient;
one or more instructions for identifying an anti-cancer agent having a defined level of efficacy in treating the cancer condition;
one or more instructions for obtaining a sample from the patient;
one or more instructions for analyzing the sample obtained from the patient to determine whether the patient is within at least one subpopulation based on at least one of gene expression data, protein expression data, or metabolite data determined from the sample;
one or more instructions for determining an alternative medical intervention for administration in association with the anti-cancer agent based at least partly on the at least one of gene expression data, protein expression data, or metabolite data determined from the sample that at least partially improves the defined level of efficacy in treating the cancer condition; and one or more instructions for displaying a treatment regimen for the anti-cancer agent and the alternative medical intervention for treating the cancer condition.

17. A method comprising:
accepting an input indicating a cancer condition associated with a patient;
identifying an anti-cancer agent having a defined level of efficacy in treating the cancer condition;
obtaining a sample from the patient;
analyzing the sample obtained from the patient to determine whether the patient is within at least one subpopulation based on at least one of gene expression data, protein expression data, or metabolite data determined from the sample;
determining an alternative medical intervention for administration in association with the anti-cancer agent based at least partly on the at least one of gene expression data, protein expression data, or metabolite data determined from the sample that at least partially improves the defined level of efficacy in treating the cancer condition; and
displaying a treatment regimen for the anti-cancer agent and the alternative medical intervention for treating the cancer condition.

18. A method comprising:
accepting an input indicating a cancer condition associated with a patient;
identifying an anti-cancer agent having a defined level of efficacy in treating the cancer condition;
collecting a blood sample from the patient;
analyzing the blood sample collected from the patient to obtain at least one of gene expression data, protein expression data, or metabolite data;
determining a treatment goal associated with the patient based on the obtained at least one of gene expression data, protein expression data, or metabolite data;
determining an alternative medical intervention for administration in association with the anti-cancer agent based at least partly on the at least one of gene expression data, protein expression data, or metabolite data determined from the sample that at least partially supports the treatment goal associated with treating the cancer condition; and
displaying a treatment regimen for the anti-cancer agent and the alternative medical intervention for treating the cancer condition.

19. A computer program product comprising:
a non-transitory signal-bearing medium bearing at least:
one or more instructions for accepting an input indicating a cancer condition associated with a patient;
one or more instructions for identifying an anti-cancer agent having a defined level of efficacy in treating the cancer condition;
one or more instructions for collecting a blood sample from the patient;
one or more instructions for analyzing the blood sample collected from the patient to obtain at least one of gene expression data, protein expression data, or metabolite data;
one or more instructions for determining a treatment goal associated with the patient based on the obtained at least one of gene expression data, protein expression data, or metabolite data;
one or more instructions for determining an alternative medical intervention for administration in association with the anti-cancer agent based at least partly on the at least one of gene expression data, protein expression data, or metabolite data determined from the sample that at least partially supports the treatment goal associated with treating the cancer condition; and
one or more instructions for displaying a treatment regimen for the anti-cancer agent and the alternative medical intervention for treating the cancer condition.

20. A system comprising:
circuitry configured for accepting an input indicating a cancer condition associated with a patient;
circuitry for identifying an anti-cancer agent having a defined level of efficacy in treating the cancer condition;
circuitry configured for collecting a blood sample from the patient;
circuitry configured for analyzing the blood sample obtained from the patient to obtain at least one of gene expression data, protein expression data, or metabolite data;
circuitry configured for determining a treatment goal associated with the patient based on the obtained at least one of gene expression data, protein expression data, or metabolite data;
circuitry for determining, based on analyzing the blood sample collected from the patient, whether the patient is exhibiting at least one symptom associated with at least one adverse event;
circuitry configured for determining an alternative medical intervention for administration in association with the anti-cancer agent based at least partly on the at least one symptom associated with the at least one adverse event and the at least one of gene expression data, protein expression data, or metabolite data determined from the sample that at least partially supports the treatment goal associated with treating the cancer condition; and
circuitry configured for displaying a treatment regimen for the anti-cancer agent and the alternative medical intervention for treating the cancer condition.

* * * * *

UNITED STATES PATENT AND TRADEMARK OFFICE
CERTIFICATE OF CORRECTION

PATENT NO. : 10,546,652 B2
APPLICATION NO. : 11/541478
DATED : January 28, 2020
INVENTOR(S) : Edward K. Y. Jung et al.

Page 1 of 1

It is certified that error appears in the above-identified patent and that said Letters Patent is hereby corrected as shown below:

In the Claims

Column 37, Line 57, Claim 9:
Replace "wherein the wherein the tissue"
With -- wherein the tissue --

Signed and Sealed this
Third Day of March, 2020

Andrei Iancu
*Director of the United States Patent and Trademark Office*